(12) United States Patent
Matsumoto et al.

(10) Patent No.: US 7,112,662 B2
(45) Date of Patent: Sep. 26, 2006

(54) ANTI-METASIN ANTIBODIES AND THEIR METHODS OF USE

(75) Inventors: Hirokazu Matsumoto, Ibaraki (JP); Yasuko Horikoshi, Ibaraki (JP); Chieko Kitada, Osaka (JP); Tetsuya Ohtaki, Ibaraki (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 65 days.

(21) Appl. No.: 10/490,125

(22) PCT Filed: Sep. 18, 2002

(86) PCT No.: PCT/JP02/09557

§ 371 (c)(1),
(2), (4) Date: Mar. 18, 2004

(87) PCT Pub. No.: WO03/027149

PCT Pub. Date: Apr. 3, 2003

(65) Prior Publication Data

US 2004/0236077 A1    Nov. 25, 2004

(30) Foreign Application Priority Data

Sep. 19, 2001   (JP) .............................. 2001-285853

(51) Int. Cl.
*C07K 16/00*   (2006.01)
(52) U.S. Cl. .............. 530/388.24; 530/387.9; 325/336; 424/139.1; 424/141.1; 424/145.1
(58) Field of Classification Search ............ 530/387.9, 530/388.24; 424/139.1, 141.1, 145.1; 435/326; 325/331
See application file for complete search history.

(56) References Cited

FOREIGN PATENT DOCUMENTS

EP   1 126 028 A1   8/2001

OTHER PUBLICATIONS

Muir et al., "AXOR12, a Novel Human G Protein-coupled Receptor, Activated by the Peptide KiSS-1", The Journal of Biological Chemistry 276 (31):28969-28975 (2001).
Ohtaki et al., "Metastasis suppressor gene KiSS-1 encodes peptide ligand of a G-protein-coupled receptor", Nature 411:613-617 (2001).
Hori et al., "Metastin Suppresses the Motility and Growth of CHO Cells Transfected with its Receptor", Biochemical and Biophysical Research Communications, 286:958-963 (2001).
West et al., "Chromosome Localization and Genomic Structure of the KiSS-1 Metastasis Suppressor Gene (KISS1)", Genomics, 54:145-148 (1998).
Kotani et al., "The Metastasis Suppressor Gene KiSS-1 Encodes Kisspeptins, the Natural Ligands of the Orphan G. Protein-coupled Receptor GPR54", The Journal of Biological Chemistry, 276(37):34631-34636 (0001).
Lee et al., "KiSS-1, a Novel Human Malignant Melanoma Metastasis-Suppressor Gene", Journal of the National Cancer Institute, 88(23): 1731-1737)1996).
Welch et al., "Molecular biology of breast cancer metastasis Genetic regulation of human breast carcinoma metastasis", Breast Cancer Res., 2:408-416 (2000).
Lee et al., "Suppression of Metastasis in Human Breast Carcinoma MDA-MB-435 Cells after Transfection with the Metastasis Suppressor Gene, KiSS-1", Cancer Research 57:2384-2387 (1997).

*Primary Examiner*—Christina Chan
*Assistant Examiner*—Michael Szperka
(74) *Attorney, Agent, or Firm*—David G. Conlin; Kathryn A. Piffat; Edwards Angell Palmer & Dodge, LLP

(57) ABSTRACT

The present invention aims at providing an antibody, by which metastin or its derivative can be quantified specifically with a high sensitivity, a method of detecting/quantifying metastin or its derivative using the antibody, and a diagnostic agent (e.g., a diagnostic for pregnancy) the same.

Specifically, an antibody capable of specifically reacting with a partial peptide at the N-terminus or C-terminus of a polypeptide having the amino acid sequence represented by SEQ ID NO: 1 or its derivative, and a method of detecting/quantifying metastin or its derivative using the antibody as well as a diagnostic agent using the same.

5 Claims, 10 Drawing Sheets a) Human Metastin : Antibody = 1:1 b) Human Metastin : Antibody = 1:10 c) Human Metastin : Antibody = 1:100

ANTI-METASIN ANTIBODIES AND THEIR METHODS OF USE

CROSS-REFERENCES TO RELATED APPLICATIONS

The present application is a 35 U.S.C. §371 national stage of PCT application PCT/JP02/09557, filed Sep. 18, 2002, which claims priority of Japanese Application Serial Number 285853/2001, filed Sep. 19, 2001, the disclosures of all of which are incorporated herein by reference.

FIELD OF THE INVENTION

The present invention relates to a novel antibody capable of specifically binding to a polypeptide having the amino acid sequence represented by SEQ ID NO: 1, or its derivatives. More specifically, the present invention relates to a method of quantifying the polypeptide or its derivatives based on the antigen-antibody reaction; an antibody useful for development of an agent for the diagnosis and prevention/treatment of diseases (cancer, and so forth) associated with the polypeptide or its derivatives, utilizing a neutralizing activity; and so forth.

BACKGROUND ART

Polypeptide having the amino acid sequence represented by SEQ ID NO: 1 (hereinafter sometimes referred to as human metastin) is a novel peptide, which was found in human placenta as a ligand to an orphan G-protein-coupled receptor protein (hOT7T175). Reportedly, human metastin has a cancer metastasis suppressing activity, because it is encoded by KiSS-1, which is a cancer metastasis suppressor gene (Nature, 411, 613–617 (2001); WO 00/24890; JPA 2000-312590). In the spontaneous metastasis model system of mouse using B16 melanoma bearing hOT7T175 forcedly expressed, a significant decrease in the number of metastin was noted when human metastin was administered, which made it clear that human metastin showed its metastasis suppressing activity also in vivo. Based on the system in which an increase in [$Ca^{2+}$] concentration in Chinese hamster ovary (hereinafter also referred to as "CHO") cells expressing the human metastin derivative hOT7T175 is used as an indicator, human metastin shows an activity equivalent to a peptide having the sequence of 45–54 amino acids in the amino acid sequence, and the C-terminal amide structure is considered to be important for the activity. Though human metastin showed a cancer metastasis suppressing activity in animal test, further detailed studies are necessary for its effects on clinical cancer in human and its physiological significance.

Any method of efficiently quantifying human metastin has not been established. Thus, in order to elucidate the physiological activities of human metastin, it has earnestly been desired to develop the assay system of detecting/quantifying human metastin in a simple manner with high sensitivity.

DISCLOSURE OF THE INVENTION

Major objects of the present invention are to provide an antibody (preferably a monoclonal antibody) capable of specifically quantifying human metastin or its derivative with high sensitivity, a method of detecting/quantifying human metastin or its derivative using the antibody, and a diagnostic (e.g., a diagnostic for pregnancy) using the same.

In order to solve the problems described above, the present inventors have made extensive investigations and as a result, have produced a plurality of monoclonal antibodies capable of specifically recognizing the N-terminus and C-terminus of human metastin or its derivative, and found that human metastin or its derivative can be detected/quantified with high sensitivity using these antibodies. The present invention has thus come to be accomplished. The present invention relates to antibodies (preferably monoclonal antibodies) capable of specifically reacting with the partial peptide of human metastin or its derivative at the C-terminus, antibodies (preferably monoclonal antibodies) capable of specifically reacting with the partial peptide of human metastin or its derivative at the N-terminus, hybridomas capable of producing the monoclonal antibodies, a method of manufacturing the antibodies and hybridomas, and an immunoassay method for human metastin or its derivative by the competitive method or the sandwich method using the antibodies.

That is, the present invention relates to the following features:

(1) An antibody capable of specifically reacting with the N-terminal region of a partial peptide in a polypeptide having the amino acid sequence represented by SEQ ID NO: 1, or its derivative;

(2) The antibody according to (1), wherein the partial peptide in the N-terminal region is a peptide having the 1–12 amino acid sequence in the amino acid sequence represented by SEQ ID NO: 1;

(3) The antibody according to (1), wherein the partial peptide in the N-terminal region is a peptide having the 1–3, 1–4, 1–5, 1–6, 1–7, 1–8 or 1–12 amino acid sequence in the amino acid sequence represented by SEQ ID NO: 1;

(4) The antibody according to (1), which does not recognize the C-terminal region of a partial peptide in a polypeptide having the amino acid sequence represented by SEQ ID NO: 1, or its derivative;

(5) The antibody according to (1), which is labeled;

(6) The antibody according to (1), which is a monoclonal antibody;

(7) The monoclonal antibody according to (6), which is shown by KIS-1Na producible from a hybridoma cell shown by KIS-1N (FERM BP-7429);

(8) An antibody capable of specifically reacting with the C-terminal region of a partial peptide in a polypeptide having the amino acid sequence represented by SEQ ID NO: 1;

(9) The antibody according to (8), wherein the partial peptide in the C-terminal region is a peptide having the 45–54 amino acid sequence in the amino acid sequence represented by SEQ ID NO: 1;

(10) The antibody according to (8), wherein the partial peptide in the C-terminal region is a peptide having the 45–54, 46–54, 47–54, 48–54, 49–54 or 50–54 amino acid sequence in the amino acid sequence represented by SEQ ID NO: 1;

(11) The antibody according to (8), which does not recognize the N-terminal region of a partial peptide in a polypeptide having the amino acid sequence represented by SEQ ID NO: 1, or its derivative;

(12) The antibody according to (8), which has a neutralizing activity to a peptide having the amino acid sequence represented by SEQ ID NO: 1, SEQ ID NO: 3, SEQ ID NO:5, SEQ ID NO:6, SEQ ID NO:7, SEQ ID NO:8 or SEQ ID NO:9;

(13) The antibody according to (8), which is labeled

(14) The antibody according to (8), which is a monoclonal antibody;

(15) The monoclonal antibody according to (14), which is shown by KIS-1Ca producible from a hybridoma cell shown by KIS-1C (FERM BP-7430);

(16) A pharmaceutical composition comprising the antibody according to (1) or (8);

(17) A diagnostic comprising the antibody according to (1) or/and (8);

(18) A method of quantifying a polypeptide having the amino acid sequence represented by SEQ ID NO: 1, or its derivative, which comprises using the antibody according to (1);

(19) The method of quantifying according to (18), which comprises using the antibody according to (8);

(20) A method for diagnosis of disease associated with a polypeptide having the amino acid sequence represented by SEQ ID NO: 1, or its derivative, which comprises using the antibody according to (1);

(21) A method for diagnosis of pregnancy, which comprises using the antibody according to (1);

(22) The method for diagnosis according to (20) or (21), which comprises further using the antibody according to (8);

(23) A method of quantifying a polypeptide having the amino acid sequence represented by SEQ ID NO: 1, or its derivative, which comprises using the antibody according to (8);

(24) A method for diagnosis of disease associated with a polypeptide having the amino acid sequence represented by SEQ ID NO: 1, or its derivative, which comprises using the antibody according to (8);

(25) A method for diagnosis of pregnancy, which comprises using the antibody according to (8);

(26) A method of quantifying a polypeptide having the amino acid sequence represented by SEQ ID NO: 1, or its derivative in a test fluid, which comprises competitively reacting the antibody according to (1) or (8) with a test fluid and a labeled form of a polypeptide having the amino acid sequence represented by SEQ ID NO: 1, or its derivative, and measuring a ratio of the labeled form of the polypeptide or its derivative bound to said antibody;

(27) A method of quantifying a polypeptide having the amino acid sequence represented by SEQ ID NO: 1, or its derivative in a test fluid, which comprises (1) reacting the antibody according to (1) immobilized on a carrier, a labeled form of the antibody according to (8) and a test fluid, and then assaying the activity of a marker, or (2) reacting the antibody according to (8) immobilized on a carrier, a labeled form of the antibody according to (1) and a test fluid, and then assaying the activity of a marker;

(28) A hybridoma cell producing the monoclonal antibody according to (6);

(29) The hybridoma cell according to (28), which is shown by KIS-1N (FERM BP-7429);

(30) A method of manufacturing the monoclonal antibody according to (6), which comprises culturing the hybridoma cell according to (28) in vivo or in vitro and collecting the monoclonal antibody according to (6) from the body fluid or culture;

(31) A hybridoma cell producing the monoclonal antibody according to (14);

(32) The hybridoma cell according to (31), which is shown by KIS-1C (FERM BP-7430);

(33) A method of producing the monoclonal antibody according to (14), which comprises culturing the hybridoma cell according to (31) in vivo or in vitro, and collecting the monoclonal antibody according to (14) from the body fluid or culture; and the like.

The present invention further provides the following features:

(i) The antibody according to (1), which specifically reacts with a peptide having the amino acid sequence represented by SEQ ID NO: 2;

(ii) The antibody according to (1), which does not recognize the partial peptide in the C-terminal region of human metastin or its derivative;

(iii) The antibody according to (8), which specifically reacts with a peptide having the amino acid sequence represented by SEQ ID NO: 3;

(iv) The antibody according to (8), which does not recognize the partial peptide in the N-terminal region of human metastin or its derivative;

(v) A method of quantifying a human metastin or its derivative in a test fluid, which comprises competitively reacting the antibody according to (1) or (8) with a test fluid and a labeled form of human metastin or its derivative, and measuring a ratio of the labeled form of the human metastin or its derivative bound to said antibody;

(vi) A method of quantifying human metastin or its derivative in a test fluid, which comprises reacting the antibody according to (1) immobilized on a carrier, a labeled form of the antibody according to (8) and a test fluid, and then assaying the activity of a marker;

(vii) A method of quantifying human metastin or its derivative in a test fluid, which comprises reacting the antibody according to (8) immobilized on a carrier, a labeled form of the antibody according to (1) and a test fluid, and then assaying the activity of a marker; and the like.

The proteins (polypeptides) of the present invention are represented in accordance with the conventional way of describing peptides, that is, the N-terminus (amino terminus) at the left hand and the C-terminus (carboxyl terminus) at the right hand. In the proteins of the present invention including the polypeptides containing the amino acid sequence shown by SEQ ID NO: 1, the C-terminus may be in any form of a carboxyl group, a carboxylate, an amide or an ester.

The derivatives of human metastin used in the present invention include those having the amino acid sequence represented by SEQ ID NO: 1 wherein a part of amino acid residues are replaced by a replaceable group(s), and so forth.

The partial peptides in the N-terminal region or the partial peptides in the C-terminal region of human metastin or its derivative, which are used in the present invention, include those wherein a part of the amino acid residues is deleted in the polypeptides having the amino acid sequence represented by SEQ ID NO: 1, those wherein a part of the amino acid residues is deleted and a part of the amino acid residues is replaced by a replaceable group(s) (e.g., Cys, hydroxyl group, and so forth), and so forth. There are employed a partial peptide wherein approximately 40 to 50 amino acids in the N-terminal region are deleted from human metastin or its derivative, a partial peptide wherein approximately 45 to 51 amino acids in the C-terminal region are deleted from human metastin or its derivative, and the like.

Specifically, the partial peptides in the N-terminal region of human metastin or its derivatives include, in the amino acid sequence represented by SEQ ID NO: 1, (i) a polypeptide having the 1–3 amino acid sequence;
(ii) a polypeptide having the 1–4 amino acid sequence;
(iii) a polypeptide having the 1–5 amino acid sequence;
(iv) a polypeptide having the 1–6 amino acid sequence;
(v) a polypeptide having the 1–7 amino acid sequence;

(vi) a polypeptide having the 1–8 amino acid sequence;
(vii) a polypeptide having the 1–12 amino acid sequence; and,
(viii) a polypeptide wherein a part of amino acid residues (e.g., one residue) in these polypeptides is replaced by a replaceable group; and so forth, and the partial peptides in the C-terminal region of human metastin or its derivatives include, in the amino acid sequence represented by SEQ ID NO: 1,
(i) a polypeptide having the 45–54 amino acid sequence;
(ii) a polypeptide having the 46–54 amino acid sequence;
(iii) a polypeptide having the 47–54 amino acid sequence;
(iv) a polypeptide having the 48–54 amino acid sequence;
(v) a polypeptide having the 49–54 amino acid sequence;
(vi) a polypeptide having the 50–54 amino acid sequence;
(vii) a polypeptide wherein a part of amino acid residues (e.g., one residue) in these polypeptides is replaced by a replaceable group; and so forth.

As the antibody of the present invention which specifically reacts with the partial peptide in the N-terminal region of human metastin or its derivatives, any antibody is usable so long as it specifically reacts with, e.g., partial peptides in the N-terminal region of human metastin or its derivatives. Preferably, the antibody is a monoclonal antibody. Specifically, there are used antibodies which antibody (preferably, a monoclonal antibody) specifically react with polypeptide [$Cys^{13}$-$NH_2$] human metastin (1–13) (SEQ ID NO: 2) having the 1–13 amino acid sequence in the amino acid sequence represented by SEQ ID NO: 1 wherein the 13 amino acid is replaced by Cys-$NH_2$, and the like. Among them, the antibodies that do not recognize the partial peptide in the C-terminal region of human metastin or its derivatives are preferred.

A preferred example is the monoclonal antibody shown by KIS-1Na.

Further as the antibodies which specifically react with the partial peptides in the N-terminal region of human metastin or its derivatives, there are used antibodies specifically recognizing (i) the 1–3 amino acid sequence, (ii) the 1–4 amino acid sequence, (iii) the 1–5 amino acid sequence, (iv) the 1–6 amino acid sequence, (v) the 1–7 amino acid sequence, (vi) the 1–8 amino acid sequence or (vii) the 1–12 amino acid sequence, of human metastin having the amino acid sequence represented by SEQ ID NO: 1; and so forth.

As the antibody of the present invention which specifically reacts with the partial peptide in the C-terminal region of human metastin or its derivatives, any antibody is usable so long as it specifically reacts with, e.g., partial peptides in the C-terminal region of human metastin or its derivatives. Specifically, there are used an antibody (preferably, a monoclonal antibody) which specifically reacts with polypeptide [$Cys^{36}$] human metastin (38–54) (SEQ ID NO: 3) having the 38–54 amino acid sequence in the amino acid sequence represented by SEQ ID NO: 1 wherein the 38 amino acid is replaced by Cys, and the like. Among them, the antibodies that do not recognize the partial peptide in the N-terminal region of human metastin or its derivatives are preferred.

More preferably, the antibodies are those neutralizing the activity of human metastin. Examples include antibodies having the neutralizing activity to a peptide having the amino acid sequence represented by SEQ ID NO: 1, SEQ ID NO: 3, SEQ ID NO: 5, SEQ ID NO: 6, SEQ ID NO: 7, SEQ ID NO: 8 or SEQ ID NO: 9.

A preferred example is a monoclonal antibody shown by KIS-1Ca.

As the antibodies specifically reacting with the partial peptide in the C-terminal region of human metastin or its derivatives, there are employed antibodies specifically recognizing (i) the 45–54 amino acid sequence, (ii) the 46–54 amino acid sequence, (iii) the 47–54 amino acid sequence, (iv) the 48–54 amino acid sequence, (v) the 49–54 amino acid sequence or (vi) the 50–54 amino acid sequence of human metastin having the amino acid sequence represented by SEQ ID NO: 1, and the like.

BEST MODE FOR CARRYING OUT THE INVENTION

Figure 1:
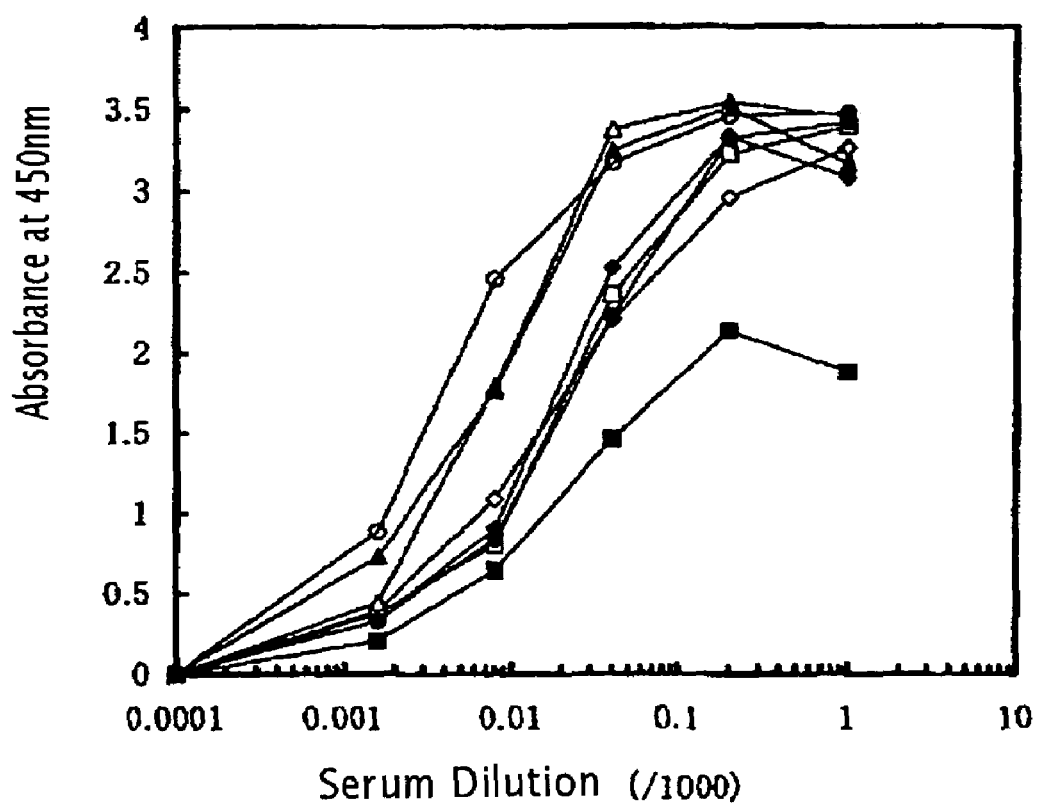
FIG. 1 shows the results of antibody titer of mouse immunized with [Cys-$NH_2^{13}$] human metastin (1–13)-KLH obtained using HRP-labeled [Cys-$NH_2^{13}$] human metastin (1–13), wherein symbols (-◇-), (-□-), (-Δ-), (-○-), (-◆-), (-■-), (-▲-) and (-●-) denote mouse No. 1 (1a), mouse No. 2 (2a), mouse No. 3 (3a), mouse No. 4 (4a), mouse No. 5 (5a), mouse No. 6 (6a), mouse No. 7 (7a) and mouse No. 8 (8a), respectively.

Hereinafter, production of antigens to the antibodies specifically reacting with the partial peptides in the N-terminal region of human metastin or its derivatives, or antibodies specifically reacting with the partial peptides in the C-terminal region of human metastin or its derivatives (hereinafter both are sometimes collectively referred to as the antibody(ies) of the present invention) as well as production of these antibodies are described.

(1) Production of Antigen

As antigens used to produce the antibodies of the present invention, any one of synthetic peptides having 1 or at least 2 antigenic determinants, which share the same determinant with, e.g., human metastin or its derivatives, may be used (hereinafter sometimes merely referred to as metastin antigen).

Human metastin or its derivatives (a) can be prepared from tissues or cells of mammals such as human, monkey, rat, mouse, and so forth by publicly known methods or their modifications, (b) can be chemically synthesized by publicly known peptide synthesis using a peptide synthesizer, and so forth, or (c) can also be prepared by culturing a transformant containing DNA encoding human metastin or its derivatives.

(a) Where metastin antigen is prepared from tissues or cells of such mammals, the tissues or cells are homogenized, the homogenate is extracted with an acid, an alcohol, and so forth and the extract is subjected to combination of salting-out, dialysis, gel filtration, chromatography techniques such as reversed phase chromatography, ion exchange chromatography, affinity chromatography, and so forth to purify/isolate metastin antigen.

(b) Where metastin antigen is chemically prepared, for example, a peptide having the same structure as that of metastin antigen purified from natural one described above, a peptide containing 1 or at least 2 of the same amino acid sequence as the amino acid sequence of at least 3, preferably at least 6 amino acids optionally located in the amino acid sequence represented by SEQ ID NO: 1, and so forth are used as the synthetic peptide.

(c) Where human metastin or its derivatives are prepared using a transformant containing DNA, the DNA can be prepared by publicly known method for cloning [e.g., the method described in Molecular Cloning, 2nd Ed., J. Sambrook et al., Cold Spring Harbor Lab. Press, 1989, and so forth]. The cloning method includes (1) a method which involves acquiring a transformant containing DNA encoding human metastin or its derivative from cDNA library by hybridization using a DNA probe or DNA primer designed based on the amino acid sequence of human metastin or its derivative; (2) a method which involves acquiring a transformant containing DNA encoding human metastin or its derivative by PCR using a DNA primer designed based on the amino acid sequence of human metastin or its derivative; and so forth.

The peptide as the metastin antigen can be prepared (1) by publicly known peptide synthesis, or (2) by cleavage of a polypeptide containing the amino acid sequence represented by SEQ ID NO: 1 with an appropriate peptidase.

For the peptide synthesis, for example, either solid phase synthesis or liquid phase synthesis may be used. That is, the partial peptides or amino acids that can construct the peptides are condensed with the remaining part. Where the product contains protecting groups, these protecting groups are removed to give the desired peptide. Publicly known methods for condensation and elimination of the protecting groups are described in (1)–(2) below.

(1) M. Bodanszky and M. A. Ondetti, Peptide Synthesis, Interscience Publishers, New York (1966)

(2) Schroeder and Luebke, The Peptide, Academic Press, New York (1965)

After the reaction, the product may be purified and isolated by a combination of conventional purification methods such as solvent extraction, distillation, column chromatography, liquid chromatography, recrystallization, and so forth to give the peptide. When the peptide obtained by the above method is in a free form, the peptide may be converted into an appropriate salt by publicly known methods; when the peptide is obtained in a salt form, it may be converted into a free form by publicly known methods.

To form amides of the peptide, commercially available resins for peptide synthesis that are suitable for amide formation may be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmethylphenyl acetamidomethyl resin, polyacrylamide resin, 4-(2',4'-dimethoxyphenyl-hydroxymethyl)phenoxy resin, 4-(2',4'-dimethoxyphenyl-Fmoc-aminoethyl) phenoxy resin, and so forth. Using these resins, amino acids, in which α-amino groups and functional groups on the side chains are appropriately protected, are condensed on the resin in the order of the sequences of the objective peptide according to various condensation methods publicly known in the art. At the end of the reaction, the peptide is excised from the resin and at the same time, the protecting groups are removed. Alternatively, the desired peptide may also be obtained by taking out the partially protected peptide using chlorotrityl resin, oxime resin, 4-hydroxybenzoic acid type resin, and so forth and removing the protecting groups in a conventional manner.

For condensation of the protected amino acids described above, a variety of activation reagents for peptide synthesis may be used, but carbodiimides are particularly preferably employed. Examples of the carbodiimides include DCC, N,N'-diisopropylcarbodiimide, N-ethyl-N'-(3-dimethylaminopropyl)carbodiimide, and so forth. For activation by these reagents, the protected amino acids in combination with a racemization inhibitor (e.g., HOBt, HOOBt) are added directly to the resin, or the protected amino acids are previously activated in the form of symmetric acid anhydrides, HOBt esters or HOOBt esters, followed by adding the thus activated protected amino acids to the resin. Solvents suitable for use to activate the protected amino acids or condense with the resin may be chosen from solvents that are known to be usable for peptide condensation reactions. Examples of such solvents are acid amides such as N,N-dimethylformamide, N,N-dimethylacetamide, N-methylpyrrolidone, and so forth; halogenated hydrocarbons such as methylene chloride, chloroform, and so forth; alcohols such as trifluoroethanol, and so forth; sulfoxides such as dimethylsulfoxide, and so forth; tertiary amines such as pyridine, and so forth; ethers such as dioxane, tetrahydrofuran, and so forth; nitrites such as acetonitrile, propionitrile, and so forth; esters such as methyl acetate, ethyl acetate, and so forth; and appropriate mixtures of these solvents. The reaction temperature is appropriately chosen from the range known to be applicable to peptide bond-forming reactions and is usually selected in the range of approximately −20° C. to 50° C. The activated amino acid derivatives are used generally in an excess of approximately 1.5 to 4 times. The condensation is examined using the ninhydrin reaction; when the condensation is insufficient, the condensation can be completed by repeating the condensation reaction without removal of the protecting groups. When the condensation is yet insufficient even after repeating the reaction, unreacted amino acids are acetylated with acetic anhydride or acetylimidazole to cancel any possible adverse affect on the subsequent reaction.

Examples of the protecting groups used to protect the starting amino groups include Z, Boc, t-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulphenyl, diphenylphosphinothioyl, Fmoc, and so forth. Examples of protecting groups for a carboxyl group include a $C_{1-6}$ alkyl group, a $C_{3-8}$ cycloalkyl group, a $C_{7-14}$ aralkyl group, 2-adamantyl, 4-nitrobenzyl, 4-methoxybenzyl, 4-chlorobenzyl, phenacyl, benzyloxycarbonyl hydrazide, t-butoxycarbonyl hydrazide, trityl hydrazide, and so forth.

The hydroxyl group of serine and threonine can be protected through, for example, its esterification or etherification. Examples of groups appropriately used for the esterification include a lower ($C_{1-6}$) alkanoyl group such as acetyl group, and so forth, an aroyl group such as benzoyl group, and so forth, and a group derived from carbonic acid such as benzyloxycarbonyl group, ethoxycarbonyl group, and so forth. Examples of a group appropriately used for the etherification include benzyl group, tetrahydropyranyl group, t-butyl group, and so forth.

Examples of groups for protecting the phenolic hydroxyl group of tyrosine include Bzl, Cl-Bzl, 2-nitrobenzyl, Br-Z, t-butyl, and so forth.

Examples of groups used to protect the imidazole moiety of histidine include Tos, 4-methoxy-2,3,6-trimethylbenzenesulfonyl, DNP, Bom, Bum, Boc, Trt, Fmoc, and so forth.

Examples of the activated carboxyl groups in the starting material include the corresponding acid anhydrides, azides, activated esters [esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)], and so forth. As the activated amino acids in which the amino groups are activated in the starting material, the corresponding phosphoric amides are employed.

To eliminate (split off) the protecting groups, there are used catalytic reduction under hydrogen gas flow in the presence of a catalyst such as Pd-black or Pd-carbon; an acid treatment with anhydrous hydrofluoric acid, methanesulfonic acid, trifluoromethanesulfonic acid or trifluoroacetic acid, or a mixture solution of these acids; a treatment with a base such as diisopropylethylamine, triethylamine, piperidine, piperazine, and so forth; reduction with sodium in liquid ammonia; and so forth. The elimination of the protecting group by the acid treatment described above is carried out generally at a temperature of approximately −20° C. to 40° C. In the acid treatment, it is efficient to add a cation scavenger such as anisole, phenol, thioanisole, m-cresol, p-cresol, dimethylsulfide, 1,4-butanedithiol or 1,2-ethanedithiol. Furthermore, 2,4-dinitrophenyl group known as the protecting group for the imidazole of histidine is removed by a treatment with thiophenol. Formyl group used as the protecting group for the indole of tryptophan is eliminated by the aforesaid acid treatment in the presence of 1,2-ethanedithiol, 1,4-butanedithiol, and so forth as well as by a treatment with an alkali such as a dilute sodium hydroxide solution, dilute ammonia, and so forth.

Protection of functional groups that should not be involved in the reaction of the starting materials, protecting groups, elimination of the protecting groups and activation of functional groups involved in the reaction may be appropriately selected from publicly known groups and publicly known means.

In another method for obtaining the amides of the peptides, for example, the α-carboxyl group of the carboxy terminal amino acid is first protected by amidation; the peptide chain is then extended from the amino group side to a desired length. Thereafter, a peptide in which only the protecting group of the N-terminal α-amino group of the peptide chain has been eliminated from the peptide and a peptide (or amino acids) in which only the protecting group of the C-terminal carboxyl group has been eliminated are prepared. The two peptides are condensed in a mixture of the solvents described above. The details of the condensation reaction are the same as described above. After the protected peptide obtained by the condensation is purified, all the protecting groups are eliminated by the method described above to obtain the desired crude peptide. This crude peptide is purified by various known purification means. Lyophilization of the major fraction gives the amide of the desired peptides.

To prepare the esterified peptides, the α-carboxyl group of the carboxy terminal amino acid is condensed with a desired alcohol to prepare the amino acid ester, which is followed by a procedure similar to the preparation of the amidated protein above to give the desired esterified peptides. The metastin antigen in its immobilized form may be provided for direct immunization. Also, the metastin antigen may be bound or adsorbed to a suitable carrier and the resulting complex may be provided for immunization. In the complex of carrier and metastin immunogen (hapten), the type of carrier and the mixing ratio of the carrier to the hapten may be any type and in any ratio, as long as the antibody efficiently works to the metastin immunogen bound or adsorbed to the carrier. Usually, a naturally occurring or synthetic high molecular weight carrier conventionally used for production of antibodies to hapten antigens is bound or adsorbed to the hapten in a weight ratio of 0.1 to 100 based on the hapten, and the bound or adsorbed product may be provided for use. As the naturally occurring high molecular weight carrier, there may be used, for example, serum albumin from mammals such as bovine, rabbit, human, and so forth, thyroglobulin from mammals such as bovine, rabbit, and so forth, hemoglobin, keyhole limpet hemocyanin, and so forth from mammals such as bovine, rabbit, human, sheep, and so forth. As the synthetic high molecular weight carrier, there may be used, for example, a variety of latexes of polymers or copolymers, and so forth, including polyamino acids, polystyrenes, polyacryls, polyvinyls, polypropylenes, and so forth.

In addition, various condensing agents can be used for coupling of the hapten and the carrier. Examples of the condensation agents which are advantageously used include diazonium compounds such as bis-diazotized benzidine which crosslinks tyrosine, histidine and tryptophan; dialdehyde compounds such as glutaraldehyde which crosslinks amino groups together; diisocyanate compounds such as toluene-2,4-diisocyanate, and so forth; dimaleimide compounds such as N,N'-o-phenylenedimaleimide which crosslinks thiol groups together; maleimide active ester compounds which crosslink amino groups and thiol groups; carbodiimide compounds which crosslink amino groups and carboxyl groups; or the like. When amino groups are crosslinked together, there may be another way in which an active ester reagent (for example, SPDP) having a dithiopyridyl group is reacted with one amino acid, followed by reduction to introduce a thiol group, whereas a maleimide group is introduced into the other amino group by the use of a maleimide active ester reagent, and then both can be reacted with each other.

(2) Production of Monoclonal Antibody

The metastin antigen is administered to warm-blooded animals either solely or together with carriers or diluents to the site where the production of antibody is possible by administration routes such as intraperitoneal injection, intravenous injection, subcutaneous injection, and so forth. In order to potentiate the antibody productivity upon the administration, complete Freund's adjuvants or incomplete Freund's adjuvants may be administered. The administration is usually carried out once every 2 to 6 weeks and approximately 2 to 10 times in total. Examples of the warm-blooded animals are monkeys, rabbits, dogs, guinea pigs, mice, rats, sheep, goats, chickens, and so forth, with the use of mice being preferred for producing monoclonal antibodies.

In the production of monoclonal antibody, a warm-blooded animal, e.g., mice, immunized with the metastin antigen wherein the antibody titer is noted is selected, then spleen or lymph node is collected after 2 to 5 days from the final immunization and antibody-producing cells contained therein are fused with myeloma cells to give anti-metastin monoclonal antibody-producing hybridomas. Measurement of the antibody titer in antisera may be carried out, for example, by reacting a labeled form of the metastin antigen, which will be later described, with the antiserum followed by assaying the binding activity of a labeling agent bound to the antibody. The fusion may be carried out, for example, by the known method by Koehler and Milstein [Nature, 256, 495 (1975)]. Examples of the fusion promoter are polyethylene glycol (PEG), Sendai virus, and so forth, of which PEG is preferably employed. Examples of the myeloma cells are NS-1, P3U1, SP2/0, AP-1, and so forth. In particular, P3U1 is preferably employed. A preferred ratio of the count of the antibody-producing cells used (spleen cells) to the count of myeloma cells is within a range of approximately 1:1 to 20:1. When PEG (preferably, PEG 1000 to PEG 6000) is added in a concentration of approximately 10 to 80% followed by culturing generally at 20 to 40° C., preferably at 30 to 37° C. for 1 to 10 minutes, an efficient cell fusion can be carried out.

Various methods can be used for screening of the anti-human metastin antibody-producing hybridomas. Examples of such methods include a method which involves adding the hybridoma supernatant to a solid phase (e.g., a microplate) adsorbed with human metastin or its derivative or its partial peptide directly or together with a carrier, adding an anti-immunoglobulin antibody (where mouse cells are used for the cell fusion, an anti-mouse immunoglobulin antibody is used) labeled with a radioactive substance or an enzyme or Protein A and detecting the anti-human metastin monoclonal antibody bound to the solid phase, and a method which comprises adding the supernatant of hybridoma to a solid phase adsorbed with an anti-immunoglobulin antibody or Protein A, adding the metastin antigen labeled with a radioactive substance or an enzyme and detecting the monoclonal antibody bound to the solid phase; and so forth. Screening and breeding of the anti-human metastin monoclonal antibody are carried out generally in a medium for animal cells (e.g., RPMI1640) supplemented with HAT (hypoxanthine, aminopterin and thymidine) containing 10–20% fetal calf serum. The antibody titer of the hybridoma culture supernatant may be assayed in a manner similar to the assay of the anti-human metastin antibody titer in antisera described above.

Separation and purification of the anti-human metastin monoclonal antibody are carried out in accordance with the separation and purification of immunoglobulins [for example, salting-out, alcohol precipitation, isoelectric point precipitation, electrophoresis, adsorption and desorption with ion exchangers (e.g., DEAE), ultracentrifugation, gel filtration, or a specific purification method which involves collecting only an antibody with an activated adsorbent such as an antigen-binding solid phase, Protein A or Protein G and dissociating the binding to obtain the antibody], as in conventional separation and purification of polyclonal antibodies.

Thus, the antibody of the present invention can be produced by culturing hybridomas in a warm-blooded animal in vivo or in vitro and collecting the antibody from the body fluid or culture.

The hybridoma producing the anti-human metastin antibody, which reacts with a part of the region in human metastin, and the hybridoma producing the anti-human metastin monoclonal antibody, which reacts with human metastin but does not react with a part of the region in human metastin, can be screened, e.g., by assaying the binding property between a peptide corresponding to a part of the region and the antibody produced by the hybridoma.

Hereinafter, the method for quantification of human metastin or its derivatives of the present invention (immunoassay) is described in more detail.

By using the antibody of the present invention, human metastin can be determined or detected by means of tissue staining, and so forth. For these purposes, the antibody molecule per se may be used, or F(ab')$_2$, Fab' or Fab fractions of the antibody molecule may be used as well.

The method of determination using the antibody of the present invention is not particularly limited, and any method may be used so far as it relates to a method, in which the amount of an antibody, antigen or antibody-antigen complex can be detected by a chemical or a physical means, in association with the amount of antigen (e.g., the amount of human metastin) in a test fluid to be assayed, and then calculated using a standard curve prepared by a standard solution containing the known amount of antigen. Advantageously used are, for example, sandwich method, competitive method, immunometric method, nephrometry, and so forth; in terms of sensitivity and specificity, the sandwich method described later is particularly preferred.

(1) Sandwich Method

The human metastin or its derivative in a sample fluid is quantified by reacting the antibody of the present invention immobilized on a carrier, a labeled form of the antibody of the present invention and the sample fluid, and then assaying the activity of a labeling agent.

Preferably, the present invention provides:

(i) a method for quantification of human metastin or its derivative in a sample fluid, which comprises reacting an antibody specifically reacting with the partial peptide in the N-terminal region of human metastin or its derivative immobilized on a carrier, an antibody specifically reacting with the partial peptide in the C-terminal region of a labeled from of human metastin or its derivative and a sample fluid, and assaying the activity of a labeling agent; and, (ii) a method for quantification of human metastin or its derivative in a sample fluid, which comprises reacting an antibody specifically reacting with the partial peptide in the C-terminal region of human metastin or its derivative immobilized on a carrier, an antibody specifically reacting with the partial peptide in the N-terminal region of a labeled from of human metastin or its derivative and a sample fluid, and assaying the activity of a labeling agent; and so forth.

More preferably, the method for quantification is the method wherein the antibody specifically reacting with the partial peptide in the N-terminal region of human metastin or its derivative is a monoclonal antibody shown by KIS-1Na and the antibody specifically reacting with the partial peptide in the C-terminal region of human metastin or its derivative is a monoclonal antibody shown by KIS-1Ca.

In the sandwich method, after a sample fluid is reacted with an immobilized form of the antibody of the present invention (primary reaction) and then reacted with a labeled form of the antibody of the present invention (secondary reaction), the activity of the labeling agent on the insoluble carrier is assayed thus, the amount of human metastin in the sample fluid can be determined. The primary and secondary reactions may be carried out, simultaneously or sequentially with intervals. The type of labeling agent and the method of immobilization may be the same as those described above. In the immunoassay by the sandwich method, it is not always required that the antibody used for the labeled antibody and for the solid phase should be one type or one species but a mixture of two or more antibodies may also be used for the purpose of improving the assay sensitivity, and so forth. In the method of assaying the human metastin by the sandwich method, where the antibody used for the primary reaction recognizes the partial peptide in the C-terminal region of human metastin or its derivative, the antibody used for the secondary reaction is preferably the antibody, which recognizes other than the partial peptide in the C-terminal region (i.e., the N-terminal region), whereas the antibody, which recognizes other than the partial peptide in the N-terminal region (i.e., the C-terminal region), is preferably used where the antibody used for the primary reaction recognizes the partial peptide in the N-terminal region of human metastin or its derivative.

Specifically, a monoclonal antibody produced using [Cys$^{13}$-NH$_2$] human metastin (1–13) as an immunogen and a monoclonal antibody using [Cys$^{38}$] human metastin (38–54) are used. These antibodies are used in the form labeled with, e.g., horseradish peroxidase (HRP).

(2) Competitive Method

The human metastin or its derivative is quantified by competitively reacting the antibody of the present invention, a test fluid and a labeled form of human metastin or its derivative, and measuring a ratio of the labeled form of the human metastin or its derivative bound to said antibody.

The reaction is carried out using, e.g., solid phase technique.

Specifically, anti-mouse IgG antibody (manufactured by ICN/CAPPEL) is used as an antibody for a solid phase, i) the antibody of the present invention (e.g., KIS-1Na or KIS-1Ca), ii) peptide represented by SEQ ID NO: 2 or SEQ ID NO: 3, which is labeled with horseradish peroxidase (HRP) and iii) a test fluid are added to a plate where the antibody for solid phase is present; after the reaction, the HRP activity adsorbed onto the solid phase is assayed to quantify the human metastin.

(3) Immunometry

In the immunometry, an antigen in a sample fluid and an antigen immobilized to a solid phase are subjected to a competitive reaction with a given amount of a labeled form of the antibody of the present invention followed by separating the solid phase from the liquid phase; or the antigen in a sample fluid is reacted with an excess amount of a labeled form of the antibody of the present invention, then an antigen immobilized to a solid phase is added thereto to bind a labeled form of the antibody of the present invention unreacted to the solid phase, followed by separating the solid phase from the liquid phase. Next, the quantity of the label in any of the phases is measured to determine the amount of the antigen in the sample fluid.

(4) Nephrometry

In the nephrometry, the amount of insoluble sediment, which is produced as a result of the antigen-antibody reaction in a gel or in a solution, is measured. When the amount of an antigen in a test sample fluid is small and only a small amount of the sediment is obtained, laser nephrometry utilizing laser scattering can be suitably used.

In (1) through (4) described above, radioisotopes, enzymes, fluorescent substances, luminescent substances, and so forth are used as labeling agents for the assay method using labeling substances. Examples of the radioisotopes are $^{125}$I, $^{131}$I, $^{3}$H, $^{14}$C, and so forth. Preferred examples of the enzymes are those that are stable and have a high specific activity, including β-galactosidase, β-glucosidase, an alkaline phosphatase, a peroxidase, malate dehydrogenase, and so forth. Examples of the fluorescent substances are fluorescamine, fluorescein isothiocyanate, and so forth. Examples of the luminescent substances are luminol, a luminol derivative, luciferin, lucigenin, and so forth. Furthermore, the biotin-avidin system may be used as well for binding of an antibody to a labeling agent.

Upon immobilization of antigens or antibodies, physical adsorption may be used. Alternatively, chemical binding that is conventionally used to immobilize or fix proteins or enzymes, and so forth may be used as well. Examples of the carrier include insoluble polysaccharides such as agarose, dextran, cellulose, and so forth; synthetic resins such as polystyrene, polyacrylamide, silicone, and so forth; glass; and the like.

In applying each of those immunoassays to the method of the present invention, it is not necessary to set up any special condition, operation, and so forth. The assay system for metastin may be built up in addition to conditions or operations conventionally used for each of the methods, taking into account the technical consideration of one skilled in the art. For the details of such conventional technical means, reference may be made to a variety of reviews, reference books, and so forth. [for example, Hiroshi Irie (ed.): "Radioimmunoassay" (published by Kodansha, 1974)]; Hiroshi Irie (ed.): "Radioimmunoassay; Second Series" (published by Kodansha, 1979); Eiji Ishikawa, et al. (ed.): "Enzyme Immunoassay" (published by Igaku Shoin, 1978); Eiji Ishikawa, et al. (ed.): "Enzyme Immunoassay" (Second Edition) (published by Igaku Shoin, 1982); Eiji Ishikawa, et al. (ed.): "Enzyme Immunoassay" (Third Edition) (published by Igaku Shoin, 1987); "Methods in Enzymology" Vol. 70 (Immunochemical Techniques (Part A)); ibid., Vol. 73 (Immunochemical Techniques (Part B)); ibid., Vol. 74 (Immunochemical Techniques (Part C)); ibid., Vol.

84 (Immunochemical Techniques (Part D: Selected Immunoassays)); ibid., Vol. 92 (Immunochemical Techniques (Part E: Monoclonal Antibodies and General Immunoassay Methods)); ibid., Vol. 121 (Immunochemical Techniques (Part I: Hybridoma Technology and Monoclonal Antibodies)) (published by Academic Press); and so forth]. Thus, when the metastin assay system of the present invention utilizing the sandwich immunoassay is built up, the method is not limited to EXAMPLES later described.

As described above, the antibody of the present invention can quantify the human metastin or its derivatives with high sensitivity, and is useful for clarification of physiological functions of human metastin and for diagnosis of diseases associated with human metastin. Specifically, the amount of human metastin or its derivative contained in body fluids (blood, plasma, serum, urine, and so forth) is determined, whereby to diagnosis is given for diseases associated with human metastin or its derivatives [e.g., cancers (e.g., skin cancer, breast cancer, colorectal cancer, colon cancer, prostate cancer, thyroid cancer, lung cancer, cervical cancer, and so forth), pregnancy induced hypertension, placental hypoplasia, threatened abortion, endometriosis, infertility, polycystic ovary syndrome, and so forth], or pregnancy, and so forth. In diagnosis of, e.g., pregnancy, the human metastin in a body fluid is quantified; where the amount of human metastin is larger than in non-pregnancy, for example, when its blood level is about 15 fmols/ml or more, preferably about 20 fmols/ml or more, pregnancy is diagnosed.

The antibody of the present invention can also be used as an agent for the prevention/treatment of diseases associated with human metastin or its derivatives [e.g., cancers (e.g., skin cancer, breast cancer, colorectal cancer, colon cancer, prostate cancer, thyroid cancer, lung cancer, cervical cancer, and so forth), pregnancy induced hypertension, placental hypoplasia, threatened abortion, endometriosis, infertility, polycystic ovary syndrome, and so forth]. In addition, the antibody is also useful for prevention of premature delivery and for reducing labor pain.

Since the agent for the treatment/prevention of the diseases described above comprising the antibody of the present invention is low toxic, it can be administered orally or parenterally to human or other warm-blooded animals (e.g., rats, rabbits, sheep, swine, bovine, cats, dogs, monkeys, and so forth) as a liquid preparation as it is, or as a pharmaceutical composition in the form of an appropriate preparation.

The dose varies depending upon subject to be administered, target disease, condition, route of administration, and so forth; in the case of using for the treatment of breast cancer in adult, it is advantageous to orally administer the antibody of the present invention in a single dose of normally about 0.01–20 mg/kg body weight, preferably about 0.1–10 mg/kg body weight, more preferably about 0.1–5 mg/kg, approximately 1 to 5 times, preferably approximately 1 to 3 times. For parenteral administration, the corresponding dose may be administered. When the conditions are extremely serious, the dose may be increased depending on the conditions.

The antibody of the present invention may be administered as it is or as an appropriate pharmaceutical composition. The pharmaceutical composition used for the administration described above contains the antibody described above or its salt, a pharmacologically acceptable carrier, and a diluent or excipient. Such a composition is provided in the preparation suitable for oral or parenteral administration.

In the specification, amino acids, and so forth are shown by abbreviations and in this case, they are denoted in accordance with the IUPAC-IUB Commission on Biochemical Nomenclature or by the common codes in the art, examples of which are shown below. For amino acids that may have the optical isomer, L form is presented unless otherwise indicated.

| | |
|---|---|
| PAM: | phenylacetamidomethyl |
| Boc: | t-butyloxycarbonyl |
| Fmoc: | 9-fluorenylmethyloxycarbonyl |
| Cl-Z: | 2-chlorobenzyloxycarbonyl |
| Br-Z: | 2-bromobenzyloxycarbonyl |
| Bzl: | benzyl |
| Cl-Bzl: | 2-chlorobenzyl |
| OcHex: | cyclohexyl ester |
| OBzl: | benzyl ester |
| Tos: | p-toluenesulfonyl |
| HONB: | N-hydroxy-5-norbornene-2,3-dicarboximido |
| HOBt: | 1-hydroxybenzotriazole |
| HOOBt: | 3-hydroxy-3,4-dihydro-4-oxo-1,2,3-benzotriazine |
| MeBzl: | 4-methylbenzyl |
| Bom: | benzyloxymethyl |
| Bum: | t-butoxymethyl |
| Trt: | trityl |
| DNP: | dinitrophenyl |
| TFA: | trifluoroacetic acid |
| DMF: | N,N-dimethylformamide |
| DCM: | dichloromethane |
| DCC: | N,N'-dichlorohexylcarbodiimide |
| BHA: | benzhydrylamine |
| pMBHA: | p-methylbenzhydrylamine |
| CHO: | formyl |
| Gly: | glycine |
| Ala: | alanine |
| Val: | valine |
| Leu: | leucine |
| Ile: | isoleucine |
| Ser: | serine |
| Thr: | threonine |
| Cys: | cysteine |
| Met: | methionine |
| Glu: | glutamic acid |
| Asp: | aspartic acid |
| Lys: | lysine |
| Arg: | arginine |
| His: | histidine |
| Phe: | phenylalanine |
| Tyr: | tyrosine |
| Trp: | tryptophan |
| Pro: | proline |
| Asn: | asparagine |
| Gln: | glutamine |
| PyBOP: | benzotriazoleoxy-tris-pyrrolidinylphosphonium hexafluorophosphate |
| PyBrop: | bromotrispyrrolidinophosphonium hexafluorophosphate |
| HOAt: | 1-hydroxy-7-azobenzotriazole |
| DIEA: | diisopropylethylamine |
| Bu$^t$: | t-butyl |
| PhSMe: | thioanisole |
| TIS: | triisopropylsilane |
| EDT: | ethanedithiol |

The sequence identification numbers used in the sequence listing of the specification indicates the amino acid sequences of the following peptides.

[SEQ ID NO: 1]

This shows the amino acid sequence of human metastin.

[SEQ ID NO: 2]

This shows the amino acid sequence of [Cys$^{13}$-NH$_2$] human metastin (1–13) manufactured by EXPERIMENT 2 (which is the 1–13 amino acid sequence in the amino acid sequence represented by SEQ ID NO: 1, wherein the 13th member is replaced by Cys-NH$_2$).

17

[SEQ ID NO: 3]

This shows the amino acid sequence of [Cys$^{38}$] human metastin (38–54) manufactured by EXPERIMENT 3 (which is the 38–541 amino acid sequence in the amino acid sequence represented by SEQ ID NO: 1, wherein the 38th member is replaced by Cys).

[SEQ ID NO: 4]

This shows the amino acid sequence of human metastin (1–54)-OH manufactured in EXPERIMENT 4 (wherein the 54th amino substituent in the amino acid sequence represented by SEQ ID NO: 1 is replaced by hydroxyl group).

[SEQ ID NO: 5]

This shows the amino acid sequence of human metastin (40–54) manufactured by EXPERIMENT 5.

[SEQ ID NO: 6]

This shows the amino acid sequence of human metastin (45–54) manufactured by EXPERIMENT 6.

[SEQ ID NO: 7]

This shows the amino acid sequence of human metastin (46–54) manufactured by EXPERIMENT 7.

[SEQ ID NO: 8]

This shows the amino acid sequence of human metastin (47–54) manufactured by EXPERIMENT 8.

[SEQ ID NO: 9]

This shows the amino acid sequence of human metastin (48–54) manufactured by EXPERIMENT 9.

The hybridoma KIS-1N obtained in EXAMPLE described below has been deposited on International Patent Organisms Depository, National Institute of Advanced Industrial Science and Technology (formerly, National Institute of Bioscience and Human-Technology (NIBH), Ministry of Economics, Trade and Industry) located at Central 6, 1-1-1 Higashi, Tsukuba, Ibaraki (postal code: 305-8566) under Accession Number FERM BP-7429 since Jan. 12, 2001.

The hybridoma KIS-1C obtained in EXAMPLE described below has been deposited on International Patent Organisms Depository, National Institute of Advanced Industrial Science and Technology (formerly, National Institute of Bioscience and Human-Technology (NIBH), Ministry of Economics, Trade and Industry) located at Central 6, 1-1-1 Higashi, Tsukuba, Ibaraki (postal code: 305-8566) under Accession Number FERM BP-7430 since Jan. 12, 2001.

The antibodies acquired from the respective hybridomas are shown by the cell names with suffix "a."

EXAMPLES

Hereinafter, the present invention will be described in more detail, with reference to EXPERIMENTS and EXAMPLES, but they are not deemed to limit the scope of the invention.

Experiment 1

Preparation of Human Metastin (SEQ ID NO: 1)

Commercially available p-methyl BHA resin (0.77 m mole/g resin) was charged in a reaction tank of peptide synthesizer ABI 430A, and the peptides: Boc-Phe, Boc-Arg (Tos), Boc-Leu, Boc-Gly, Boc-Phe, Boc-Ser(Bzl), Boc-Asn, Boc-Trp(CHO), Boc-Asn, Boc-Tyr(Br-Z), Boc-Asn, Boc-Pro, Boc-Leu, Boc-Asp(OcHex), Boc-Lys(Cl-Z), Boc-Glu (OcHex), Boc-Arg(Tos), Boc-Gln, Boc-Val, Boc-Leu, Boc-Val, Boc-Ala, Boc-Gly, Boc-Gln, Boc-Pro, Boc-Ala, Boc-Pro, Boc-Ile, Boc-Gln, Boc-Arg(Tos), Boc-Ser(Bzl), Boc-His(Bom), Boc-Pro, Boc-Ala, Boc-Ser(Bzl), Boc-Leu, Boc-Gly, Boc-Pro, Boc-Gln, Boc-Gln, Boc-Arg(Tos), Boc-Ser (Bzl), Boc-Gly, Boc-Ser(Bzl), Boc-Ser(Bzl), Boc-Glu (OcHex), Boc-Pro, Boc-Pro, Boc-Pro, Boc-Ser(Bzl), Boc-Leu, Boc-Ser(Bzl), Boc-Thr(Bzl), Boc-Gly were sequentially introduced in the order given above by the Boc-strategy (NMP-HOBt) peptide synthesis process to give the objective protected peptide resin. After 0.1 g of this resin was stirred in 10 ml of anhydrous hydrofluoric acid at 0° C. for 60 minutes together with 1 ml of p-cresol and 1 ml of 1,4-butanediol, the hydrofluoric acid was distilled off in vacuum. Diethyl ether was added to the residue and the precipitates were taken by filtration. To the precipitates, 50% acetic acid aqueous solution was added for extraction. After insoluble matters were removed, the extract was thoroughly concentrated and the concentrate was passed through Sephadex (trademark) G-25 column (2.0×80 cm) filled up with 50% acetic acid aqueous solution, which was developed with the same solvent. Major fractions were collected and lyophilized to give 33 mg of white powders. A half aliquot of the powders was applied on a column (1×1 cm) filled up with CM-Cellulofine (registered trademark), which was eluted with a gradient of $CH_3CONH_4$. Major fractions were collected and passed through reverse phase chromatography column (2.6×60 cm) packed with Li Chroprep (trademark) RP-18. The column was washed with 200 ml of 0.1% TFA/water. Linear density gradient elution was performed using 300 ml of 0.1% TFA/water and 300 ml of 0.1% TFA-containing 33% acetonitrile in water. Major fractions were collected and lyophilized to give 2.2 mg of the desired peptide. The resulting peptide was analyzed by mass spectrometry. By the mass spectrometry, $(M+H)^+$ was found to be 5858.5 daltons (calcd. 5858.5 daltons)

Conditions for purification:
Elution time on HPLC: 9.7 mins.

Column Conditions
Column: Wakosil 5C18T 4.6×100 mm
Eluants: elution in a linear density gradient of A/B=95/5–45/55, using eluant A —0.1% TFA/water, eluant B —0.1% TFA-containing acetonitrile (25 mins.)
Flow rate: 1.0 ml/mins.

Experiment 2

Production of [Cys$^{13}$-NH$_2$] Human Metastin (1–13) (SEQ ID NO: 2)

To 403 mg of Sieber amide resin (registered trademark), 10 mL of 5% piperidine/DCM/DMF (1/1) was added, and after stirring for 10 minutes, 10 mL of 20% piperidine/DMF was replaced for the 5% piperidine, followed by stirring for further 20 minutes. After 439 mg of Fmoc-Cys (Trt), 390 mg of PyBOP, 101 mg of HOBt, 393 mL of DIEA and 5 mL of DMF were added, the mixture was stirred for an hour. After the resin was washed, 439 mg of Fmoc-Cys (Trt), 350 mg of PyBrop, 102 mg of HOAt, 393 mL of DIEA and 5 mL of DMF were added to the resin, followed by stirring for an hour. After the resin was washed, 118 mL of Ac2O, 87 mL of DIEA and 5 mL of DCM were added to the resin and the mixture was stirred for an hour. The resin was washed to give Fmoc-Cys(Trt)-Sieber amide resin. The amount of Fmoc-Cys(Trt) introduced into this resin was 0.43 mmol/g.

Using this resin as the starting material, Fmoc-protected amino acid derivatives were condensed on an ABI 433A peptide synthesizer in the order of the amino acid sequence of the objective peptide to extend the peptide chain. Thus, 726 mg of Fmoc-Gly Thr(Bu$^t$) Ser(Bu$^t$) Leu Ser(Bu$^t$) Leu Ser(Bu$^t$) Pro Pro Pro Glu(OBu$^t$) Ser(Bu$^t$) Ser(Bu$^t$) Gly Cys(Trt)-Sieber amide resin was obtained (SEQ ID NO: 10). Next, 5 mL of 20% piperidine/DMF was added to 218 mg of this resin, followed by stirring for 30 minutes. After the resin was washed, 2 mL of TFA/PhSMe/m-cresol/TIS/EDT (85/5/5/2.5/2.5) was added to the resin, followed by stirring for 2 hours. The resin was removed by filtration and washed with ether to give the precipitate (71.2 mg). A 25 mg aliquot was purified on HPLC to give 13.4 mg of the objective product. The peptide obtained was subjected to mass spectrometry. By the mass spectrometry, (M+H)$^+$ was fond to be 1217.3 daltons (calcd. 1217.5 daltons).

Conditions for Purification:
Elution time on HPLC: 12.7 mins.

Column Conditions
  Column: Wakosil-II 5C18 HG 4.6×100 mm
  Eluants: elution in a linear density gradient of A/B=100/0–30/70, using eluant A—0.1% TFA/water and eluant B—0.1% TFA-containing acetonitrile (35 mins.)
  Flow rate: 1.0 ml/mins.

Experiment 3

Production of [Cys$^{38}$] Human Metastin (38–54) (SEQ ID NO: 3)

Commercially available p-methyl BHA resin (0.77 m mole/g resin) was charged in a reaction tank of peptide synthesizer ABI 430A, and the peptides: Boc-Phe, Boc-Arg(Tos), Boc-Leu, Boc-Gly, Boc-Phe, Boc-Ser(Bzl), Boc-Asn, Boc-Trp(CHO), Boc-Asn, Boc-Tyr(Br-Z), Boc-Asn, Boc-Pro, Boc-Leu, Boc-Asp(OcHex), Boc-Lys(Cl-Z), Boc-Glu(OcHex) and Boc-Cys (4MeBzl) were sequentially introduced in the order given above by the Boc-strategy (NMP-HOBt) peptide synthesis process to give the objective protected peptide resin. After 0.23 g of this resin was stirred in 10 ml of anhydrous hydrofluoric acid at 0° C. for 60 minutes together with 1 ml of p-cresol and 1.2 ml of 1,4-butanediol, the hydrofluoric acid was removed by distillation in vacuum and diethyl ether was added to the residue. The precipitate was taken out by filtration and 50% acetic acid aqueous solution was added to the precipitate for extraction. After insoluble matters were removed, the extract was thoroughly concentrated. The concentrate was applied on Sephadex (trademark) G-25 column (2.0×80 cm) filled up with 50% acetic acid aqueous solution, which was developed with the same solvent. Major fractions were collected and lyophilized to give 98 mg of white powders. A 20 mg aliquot was applied on a reverse phase chromatography column (2.6×60 cm) packed with Li Chroprep (trademark) RP-18. After washing with 200 ml of 0.1% TFA/water, linear density gradient elution was carried out using 300 ml of 0.1% TFA/water and 300 ml of 0.1% TFA-containing 40% acetonitrile/water. Major fractions were collected and lyophilized to give 7 mg of the objective peptide. The peptide obtained was analyzed by mass spectrometry. By the mass spectrometry, (M+H)$^+$ was found to be 2102.1 daltons (calcd. 2101.99 daltons).

Conditions for Purification:
Elution time on HPLC: 10.3 mins.

Column Conditions
  Column: Wakosil 5C18T 4.6×100 mm
  Eluants: elution in a linear density gradient of A/B=80/20–60/40, using eluant A—0.1% TFA/water and eluant B—0.1% TFA-containing acetonitrile (10 mins.)
  Flow rate: 1.0 ml/mins.

Experiment 4

Preparation of Human Metastin (1–54)OH (SEQ ID NO: 4)

Commercially available Boc-Phe-OCH2-PAM resin (0.77 m mole/g resin) was charged in a reaction tank of a peptide synthesizer ABI 430A, and the peptides: Boc-Arg(Tos), Boc-Leu, Boc-Gly, Boc-Phe, Boc-Ser(Bzl), Boc-Asn, Boc-Trp(CHO), Boc-Asn, Boc-Tyr(Br-Z), Boc-Asn, Boc-Pro, Boc-Leu, Boc-Asp(OcHex), Boc-Lys(Cl-Z), Boc-Glu(OcHex), Boc-Arg(Tos), Boc-Gln, Boc-Val, Boc-Leu, Boc-Val, Boc-Ala, Boc-Gly, Boc-Gln, Boc-Pro, Boc-Ala, Boc-Pro, Boc-Ile, Boc-Gln, Boc-Arg(Tos), Boc-Ser(Bzl), Boc-His(Bom), Boc-Pro, Boc-Ala, Boc-Ser(Bzl), Boc-Leu, Boc-Gly, Boc-Pro, Boc-Gln, Boc-Gln, Boc-Arg(Tos), Boc-Ser(Bzl), Boc-Gly, Boc-Ser(Bzl), Boc-Ser(Bzl), Boc-Glu(OcHex), Boc-Pro, Boc-Pro, Boc-Pro, Boc-Ser(Bzl), Boc-Leu, Boc-Ser(Bzl), Boc-Thr(Bzl) and Boc-Gly were sequentially introduced in the order given above by the Boc-strategy (NMP-HOBt) peptide synthesis process to give the objective protected peptide resin. The peptide was treated as in the production of the peptide shown by SEQ ID NO: 1. The peptide obtained was analyzed by mass spectrometry. By the mass spectrometry (M+H)$^+$ was found to be 5859.3 daltons (calcd. 5859.6 daltons).

Conditions for Purification:
Elution time on HPLC: 10.0 mins.

Column Conditions
  Column: Wakosil 5C18T 4.6×100 mm
  Eluants: elution in a linear density gradient of A/B=95/5–45/55, using eluant A—0.1% TFA/water and eluant B—0.1% TFA-containing acetonitrile (25mins.)
  Flow rate: 1.0 ml/mins.

Experiment 5

Preparation of Human Metastin (40–54) (SEQ ID NO: 5)

Commercially available p-methyl BHA resin (0.77 m mole/g resin) was charged in a reaction tank of a peptide synthesizer ABI 430A, and the peptides: Boc-Phe, Boc-Arg(Tos), Boc-Leu, Boc-Gly, Boc-Phe, Boc-Ser(Bzl), Boc-Asn, Boc-Trp(CHO), Boc-Asn, Boc-Tyr(Br-Z), Boc-Asn, Boc-Pro, Boc-Leu, Boc-Asp(OcHex) and Boc-Lys(Cl-Z) were sequentially introduced in the order given above by the Boc-strategy (NMP-HOBt) peptide synthesis process to give the objective protected peptide resin. After 0.12 g of this resin was stirred in 10 ml of anhydrous hydrofluoric acid at 0° C. for 60 minutes together with 1 ml of p-cresol and 1.2 ml of 1,4-butanediol, the hydrofluoric acid was removed by distillation in vacuum and diethyl ether was added to the residue. To the precipitate 50% acetic acid aqueous solution was added for extraction. After insoluble matters were removed, the extract was thoroughly concentrated. The concentrate was then applied on Sephadex (trademark) G-25 column (2.0×80 cm) filled up with 50% acetic acid aqueous solution, which was developed with the same solvent. Major fractions were collected and lyophilized to give 40 mg of white powders. A half aliquot of the powders was applied on a reverse phase chromatography column (2.6×60 cm) packed with Li Chroprep (trademark) RP-18. After washing with 200 ml of 0.1% TFA/water, linear density gradient elution was carried out using 300 ml of 0.1% TFA/water and 300 ml of 0.1% TFA-containing 33% acetonitrile/water. Major fractions were collected and lyophilized to give 4.1 mg of the objective peptide. The peptide obtained was analyzed by mass spectrometry. By the mass spectrometry, (M+H)⁺ was found to be 1869.9 daltons (calcd. 1969.9 daltons)

Conditions for Purification:
Elution time on HPLC: 18.6 mins.

Column Conditions
  Column: Wakosil 5C18T 4.6×100 mm
  Eluants: elution in a linear density gradient with A/B=95/5–45/55, using eluant A—0.1% TFA/water and eluant B—0.1% TFA-containing acetonitrile (25 mins.)
  Flow rate:1.0 ml/min.

Experiment 6

Preparation of Human Metastin (45–54) (SEQ ID NO: 6)
Commercially available p-methyl BHA resin (0.77 m mole/g resin) was charged in a reaction tank of a peptide synthesizer ABI 430A, and the peptides: Boc-Phe, Boc-Arg (Tos), Boc-Leu, Boc-Gly, Boc-Phe, Boc-Ser(Bzl), Boc-Asn, Boc-Trp(CHO), Boc-Asn and Boc-Tyr(Br-Z) were sequentially introduced in the order given above by the Boc-strategy (NMP-HOBt) peptide synthesis process to give the objective protected peptide resin. A 0.11 g aliquot of this resin was treated in a manner similar to EXPERIMENT 1 to remove the protective groups, which was then purified to give 2.2 mg of the objective peptide. The peptide obtained was analyzed by mass spectrometry. By the mass spectrometry, $(M+H)^+$ was found to be 1302.5 daltons (calcd. 1302.6 daltons).

Conditions for Purification:
Elution time on HPLC: 18.7 mins.

Column Conditions
  Column: Wakosil 5C18T 4.6×100 mm
  Eluants: elution in a linear density gradient of A/B=95/5–45/55, using eluant A—0.1% TFA/water and eluant B—0.1% TFA-containing acetonitrile (25 mins.)
  Flow rate: 1.0 ml/mins.

Experiment 7

Preparation of Human Metastin (46–54) (SEQ ID NO: 7)
Commercially available p-methyl BHA resin (0.77 m mole/g resin) was charged in a reaction tank of a peptide synthesizer ABI 430A, and the peptides: Boc-Phe, Boc-Arg (Tos), Boc-Leu, Boc-Gly, Boc-Phe, Boc-Ser(Bzl), Boc-Asn, Boc-Trp(CHO) and Boc-Asn were sequentially introduced in the order given above by the Boc-strategy (NMP-HOBt) peptide synthesis process to give the objective protected peptide resin. A 0.11 g aliquot of this resin was treated in a manner similar to EXPERIMENT 1 to remove the protective groups, which was then purified to give 3.4 mg of the objective peptide. The peptide obtained was analyzed by mass spectrometry. By the mass spectrometry, $(M+H)^+$ was found to be 1139.6 daltons (calcd. 1139.6 daltons).

Conditions for purification: Elution time on HPLC: 18.1 mins. Column conditions Column: Wakosil 5C18T 4.6×100mm Eluants: elution in a linear density gradient of A/B=95/5–45/55, using eluant A—0.1% TFA/water and eluant B—0.1% TFA-containing acetonitrile (25 mins.)
  Flow rate: 1.0 ml/mins.

Experiment 8

Preparation of Human Metastin (47–54) (SEQ ID NO: 8)
Commercially available p-methyl BHA resin (0.77 m mole/g resin) was charged in a reaction tank of a peptide synthesizer ABI 430A, and the peptides: Boc-Phe, Boc-Arg (Tos), Boc-Leu, Boc-Gly, Boc-Phe, Boc-Ser(Bzl), Boc-Asn and Boc-Trp(CHO) were sequentially introduced in the order given above by the Boc-strategy (NMP-HOBt) peptide synthesis process to give the objective protected peptide resin. A 0.12 g aliquot of this resin was treated in a manner similar to EXPERIMENT 1 to remove the protective groups, which was then purified to give 13.0 mg of the objective peptide. The peptide obtained was analyzed by mass spectrometry. By the mass spectrometry, $(M+H)^+$ was found to be 1025.5 daltons (calcd. 1025.5).

Conditions for Purification:
Elution time on HPLC:17.6 min

Column Conditions
  Column: Wakosil 5C18T 4.6×100 mm
  Eluants: elution in a linear density gradient of A/B=95/5–45/55, using eluant A—0.1% TFA/water and eluant B—0.1% TFA-containing acetonitrile (25 mins.)
  Flow rate: 1.0 ml/mins.

Experiment 9

Preparation of Human Metastin (48–54) (SEQ ID NO: 9)
Commercially available p-methyl BHA resin (0.77 m mole/g resin) was charged in a reaction tank of a peptide synthesizer ABI 430A and the peptides: Boc-Phe, Boc-Arg (Tos), Boc-Leu, Boc-Gly, Boc-Phe, Boc-Ser(Bzl) and Boc-Asn were sequentially introduced in the order given above by the Boc-strategy (NMP-HOBt) peptide synthesis process to give the objective protected peptide resin. After the resin was stirred in 10 ml of anhydrous hydrofluoric acid at 0° C. for 60 minutes together with 1 ml of p-cresol, the mixture was treated and purified in a manner similar to EXPERIMENT 1 to give 29.0 mg of the objective peptide. The peptide obtained was analyzed by mass spectrometry. By the mass spectrometry, $(M+H)^+$ was found to be 839.5 daltons (calcd. 839.5 daltons).

Conditions for Purification:
Elution time on HPLC: 15.6 mins

Column Conditions
  Column: Wakosil 5C18T 4.6×100mm
  Eluants: elution in a linear density gradient of A/B=95/5–45/55, using eluant A—0.1% TFA/water and eluant B—0.1% TFA-containing acetonitrile (10 mins.)
  Flow rate: 1.0 ml/mins.

Experiment 10

Production of Immunogen (1) Production of Immunogen Containing [$Cys^{13}$-$NH_2$] Human Metastin (1–13)
A complex of [$Cys^{13}$-$NH_2$] human metastin (1–13) obtained in EXPERIMENT 2 and Keyhole Limpet Hemocyanin (KLH) was produced and used as an immunogen.

That is, 20 mg of KLH was dissolved in 1.4 ml of 0.1M phosphate buffer (pH 6.5). The solution was mixed with 100 μl of DMF solution containing 2.2 mg (8 μmols) of N-(γ- maleimidobutyroxy)succinimide (GMBS) followed by reacting them at room temperature for 40 minutes. After the reaction, the mixture was fractionated on a Sephadex G-25 column and mixed with 15 mg of maleimido-introduced KLH and 3.75 mg of [$Cys^{13}$-$NH_2$] human metastin (1–13). The mixture was reacted at 4° C. for 2 days. After the reaction, the mixture was dialyzed to physiological saline at 4° C. for 2 days.

(2) Production of Immunogen Containing [$Cys^{38}$] Human Metastin (38–54)

A complex of [$Cys^{38}$] human metastin (38–54) obtained in EXPERIMENT 3 and KLH was produced and used as an immunogen.

That is, 21 mg of KLH was dissolved in 1.4 ml of 0.1M phosphate buffer (pH 6.5). The solution was mixed with 100 μl of DMF solution containing 2.35 mg (8.4 μmols) of GMBS followed by reacting them at room temperature for 40 minutes. After the reaction, the mixture was fractionated on a Sephadex G-25 column and mixed with 15 mg of maleimido-introduced BTG and 3.0 mg of [$Cys^{38}$] human metastin (38–54). The mixture was reacted at 4° C. overnight. After the reaction, the mixture was dialyzed to physiological saline at 4° C. for 3 days.

Experiment 11

Immunization

BALB/C female mice of 6 to 8 weeks old were immunized subcutaneously with the immunocomplexes [$Cys^{13}$-$NH_2$] human metastin (1–13)-KLH and [$Cys^{38}$] human metastin (38–54)-KLH obtained in EXPERIMENT 10, respectively, in a dose of 50 μg/mouse, together with complete Freund's adjuvant. Since then, the animals were boostered 2 or 3 times with the same dose of the immunogen every 3 other weeks.

Experiment 12

Preparation of Enzyme-Labeled Antigen (1) Preparation of Horseradish Peroxidase (HRP)-Labeled [$Cys^{13}$-$NH_2$] Human Metastin (1–13)

[$Cys^{13}$-$NH_2$] Human metastin (1–13) obtained in EXPERIMENT 2 was crosslinked with HRP (for enzyme immunoassay; manufactured by Boehringer Mannheim GmbH), which was made a label for enzyme immunoassay (EIA). That is, 6 mg (150 nmols) of HRP was dissolved in 0.95 ml of 0.1M phosphate buffer (pH 6.5) and the solution was mixed with 50 μl of DMF solution containing 0.42 mg (1.5 μmols) of GMBS. After they were reacted at room temperature for 30 minutes, the mixture was fractionated on a Sephadex G-25 column. The thus prepared maleimido-introduced HRP, 4.2 mg ($10^6$ nmols), and 0.98 mg (319 nmols) of [$Cys^{13}$-$NH_2$] human metastin (1–13) obtained in EXPERIMENT 2 were mixed and reacted at 4° C. for a day. After the reaction, the mixture was fractionated on an Ultrogel AcA44 (manufactured by LKB-Pharmacia) column to give HRP-labeled [$Cys^{13}$-$NH_2$] human metastin (1–13).

(2) Production of HRP-Labeled [Cys38] Human Metastin (38–54)

[$Cys^{38}$] Human metastin (38–54) obtained in EXPERIMENT 3 was crosslinked with HRP, which was made a label for EIA. That is, 8 mg (203 nmols) of HRP was dissolved in 1.4 ml of 0.1M phosphate buffer (pH 6.5) and the solution was mixed with 100 μl of DMF solution containing 0.56 mg (2.02 μmols) of GMBS. After they were reacted at room temperature for 30 minutes, the mixture was fractionated on a Sephadex G-25 column. The thus prepared maleimido-introduced HRP, 6.0 mg (142 nmols), and 0.89 mg (425 nmols) of [$Cys^{38}$] human metastin (38–54) obtained in EXPERIMENT 3 were mixed and reacted at 4° C. for a day. After the reaction, the mixture was fractionated on an Ultrogel AcA44 column to give HRP-labeled [$Cys^{38}$] human metastin (38–54).

Experiment 13

Assay for Antibody Titer (1) Assay for Antibody Titer in Antisera of Mice Immunized with [$Cys^{13}$-$NH_2$] Human Metastin (1–13)-KLH Complex Immunization was made twice with the [$Cys^{13}$-$NH_2$] human metastin (1–13)-KLH complex with 3 week intervals. A week after the immunization, blood was drawn from the fundus oculi to collect blood. After the blood was further centrifuged at 4° C. in 12,000 rpm for 15 minutes, the supernatant was recovered to obtain antisera. The antibody titer in the antisera was assayed by the following procedure. In order to prepare an anti-mouse immunoglobulin antibody-bound microplate, a 100 μl aliquot of 0.1M carbonate buffer (pH 9.6) containing 100 μg/ml of anti-mouse immunoglobulin antibody (IgG fraction, manufactured by CAPPEL) was dispensed in each well of a 96-well microplate, which was allowed to stand at 4° C. for 24 hours. Next, after the plate was washed with phosphate buffered saline (PBS, pH7.4), a 300 μl aliquot of PBS containing 25% Block Ace (manufactured by Snow Brand Milk Products) was dispensed in each well and treated at 4° C. for at least 24 hours to block redundant binding sites. After 50 μl of Buffer C [0.02M phosphate buffer, pH 7.0, containing 1% BSA, 0.4M NaCl, 0.05% 2 mM EDTA.Na (ethylenediamine-N,N,N',N'-tetraacetic acid, disodium salt, dihydrate), DOJINDO Co.] and 100 μl of antisera to the complex diluted with Buffer C were added to each well of the anti-mouse immunoglobulin antibody-bound microplate obtained, the reaction was carried out at 4° C. for 16 hours. Next, the plate was washed with PBS and 100 μl of HRP-labeled [$Cys^{13}$-$NH_2$] human metastin (1–13) (diluted to 300-fold with Buffer C) prepared in EXPERIMENT 12 (1) was added thereto and the reaction was carried out at room temperature for a day. Then, the plate was washed with PBS and 100 μl of TMB Microwell Peroxidase Substrate System (KIRKEGAARD & PERRY LAB, INC., consigned to Funakoshi Co., Ltd.) was added and the reaction was carried out at room temperature for 10 minutes to assay the enzyme activity on a solid phase. After the reaction was terminated by adding 100 μl of 1M phosphoric acid, the absorption was measured at 450 nm using a plate reader (BICHROMATIC, manufactured by Dainippon Pharmaceutical Co., Ltd.).

The results are shown in FIG. 1. An increase of the antibody titer to [$Cys^{13}$-$NH_2$] human metastin (1–13) was noted in antisera to the complex of all of the 8 mice immunized.

(2) Assay for Antibody Titer in Antisera of Mice Immunized with [$Cys^{38}$] Human Metastin (38–54)-KLH Complex Immunization was made 3 times with the [$Cys^{38}$] human metastin (38–54)-KLH complex. A week after the immunization, blood was drawn from the fundus oculi to collect blood. After the blood was further centrifuged at 4° C. in 12,000 rpm for 15 minutes, the supernatant was recovered to obtain antisera. The antibody titer in the antisera was assayed by the following procedure.

After 50 μl of Buffer C and 100 μl of antisera diluted with Buffer C were added to each well of the anti-mouse immunoglobulin antibody-bound microplate prepared (1) above, the reaction was carried out at 4° C. for 16 hours. Next, the plate was washed with PBS and 100 μl of HRP-labeled [Cys$^{38}$] human metastin (38–54) (diluted to 500-fold with Buffer C) prepared in EXPERIMENT 12 (2) was added, and the mixture was reacted at room temperature for a day. Then, the plate was washed with PBS and 100 μl of TMB Microwell Peroxidase Substrate System (KIRKEGAARD & PERRY LAB, INC., consigned to Funakoshi Co., Ltd.) was added and the reaction was carried out at room temperature for 10 minutes to assay the enzyme activity on a solid phase. After the reaction was terminated by adding 100 μl of 1M phosphoric acid, the absorption was measured at 450 nm using a plate reader (BICHROMATIC, manufactured by Dainippon Pharmaceutical Co., Ltd.).

Figure 2:
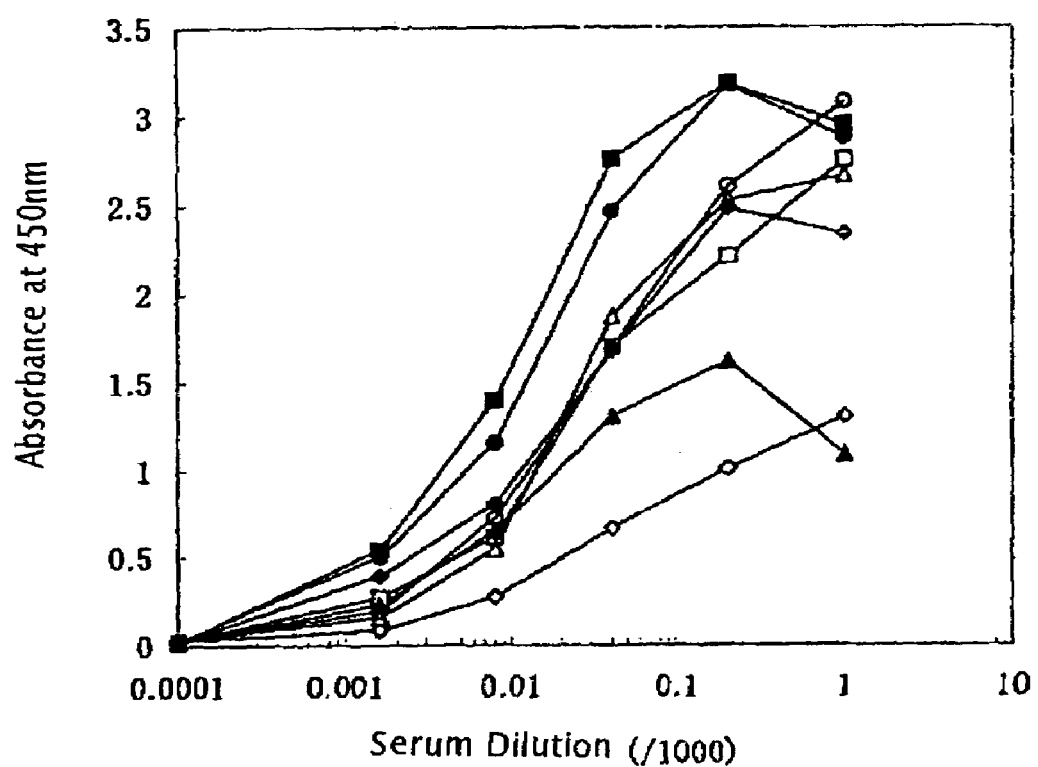
FIG. 2 shows the results of antibody titer of mouse immunized with [$Cys^{38}$] human metastin (38–54)-KLH obtained using HRP-labeled [$Cys^{38}$] human metastin (38–54), wherein symbols (-◇-), (-□-), (-Δ-), (-○-), (-◆-), (-■-), (-▲-) and (-●-) denote mouse No. 1 (1a), mouse No. 2 (2a), mouse No. 3 (3a), mouse No. 4 (4a), mouse No. 5 (5a), mouse No. 6 (6a), mouse No. 7 (7a) and mouse No. 8 (8a), respectively.

The results are shown in FIG. 2. An increase of the antibody titer to [Cys$^{38}$] human metastin (38–54) was noted in antisera to the complex of all of the 8 mice immunized.

Example 1

Preparation of Monoclonal Anti-Human Metastin Antibody

A solution of 200–300 μg of the immunogen in 0.25–0.3 ml of physiological saline was inoculated to a mouse showing a relatively high antibody titer in the vein to achieve the final immunization. Three or four days after the final immunization, the spleen was withdrawn from the mouse, pressed against a stainless mesh, filtered and suspended in Eagle's minimum essential medium (MEM) to give the spleen cell suspension. As cells used for cell fusion, BALB/C mouse-derived myeloma cell P3-X63.Ag8.U1(P3U1) was used [Current Topics in Microbiology and Immunology, 81, 1, 1978].

The cell fusion was performed by a modification of the original method [Nature, 256, 495, 1975]. That is, spleen cells and P3U1 were washed 3 times with serum-free MEM, respectively, and they were blended to be in a 10:1 proportion of the spleen cells and P3U1 in cell count. The mixture was centrifuged at 800 rpm for 15 minutes to deposit the cells. After the supernatant was thoroughly removed, the deposit was lightly unraveled and 0.3 ml of 45% polyethylene glycol (PEG) 6000 (manufactured by Kochlight) was added thereto. The mixture was allowed to stand for 7 minutes in a warm water bath of 37° C. to perform cell fusion. The fusion was followed by addition of MEM to the cells in a rate of 2 ml/min. When MEM added reached 15 ml in total, the mixture was centrifuged at 600 rpm for 15 minutes and the supernatant was removed. The cell deposit was suspended in 10% fetal calf serum-containing GIT medium (Wako Pure Chemical Industries, Ltd. (GIT-10% FCS) in 2×10$^5$, and the suspension was plated on 192 wells of a 24-well Multidish (manufactured by Limbro) in 1 ml/well. After the plating, the cells were incubated at 37° C. in a 5% carbonic acid incubator. Twenty-four hours after, GIT-10% FCS medium (HAT medium) containing HAT (1×10$^{-4}$ M hypoxanthine, 4×10$^{-7}$ M aminopterin, 1.6×10$^{-3}$ M thymidine) was added to the cells in 1 ml/well, thereby to start HAT selective culture. The HAT selective culture was continued by discarding the old medium on Days 3, 6 and 9 after start of the incubation and supplementing 1 ml of HAT medium. Proliferation of the hybridoma was noted on Days 9–14 after the cell fusion. When the culture medium turned yellow (ca. 1×10$^6$ cells/ml), the supernatant was collected and the antibody titer was assayed in accordance with the procedure described in EXPERIMENT 13.

Figure 3:
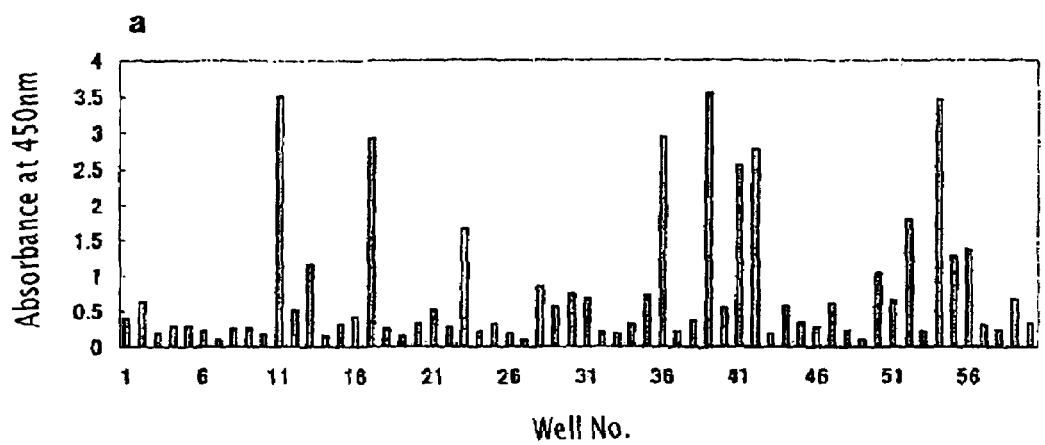
FIG. 3 shows a typical example of the screening of hybridoma after cell fusion when mouse immunized with [Cys-$NH_2^{13}$] human metastin (1–13)-KLH was used.
Figure 3:
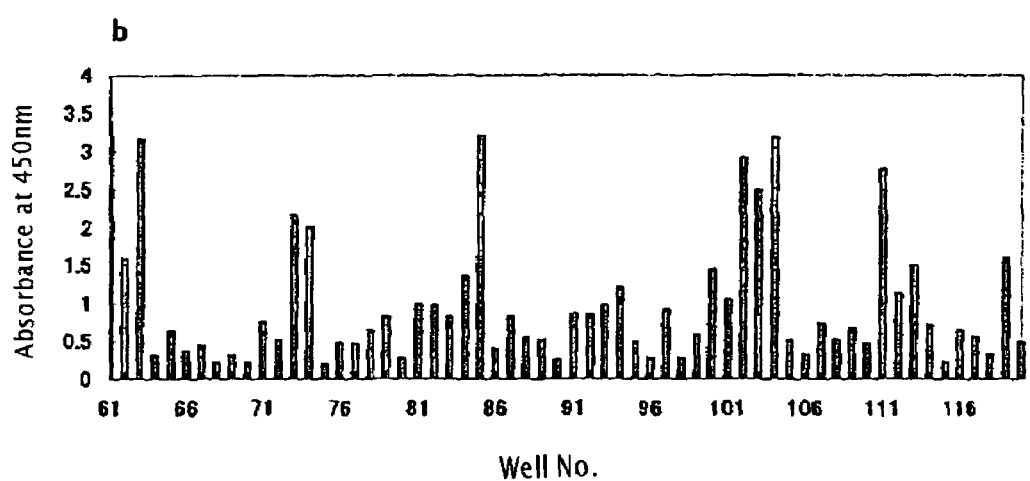
Figure 3:
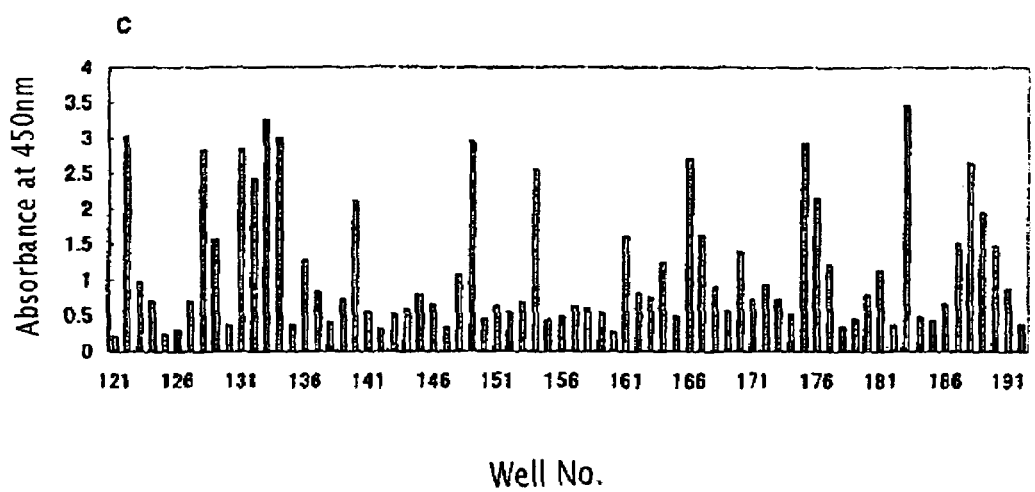

As an example where the antibody producing cell lines of hybridomas derived from the mice immunized with [Cys$^{13}$-NH$_2$] human metastin (1–13)-KLH were selected, the antibody-producing conditions of the hybridomas obtained by cell fusion using mice Nos. 3 and 4 (cf. FIG. 1) are shown in FIG. 3. The following 5 hybridomas in total were selected from the antibody-producing hybridomas acquired (TABLE 1).

TABLE 1

Reactivity of anti-human [Cys$^{13}$-NH$_2$] human metastin (1–13) monoclonal antibody Reactivity[1)]

| Hybridoma No. | Human metastin (1–54) | Class/Subclass | Notes |
| --- | --- | --- | --- |
| 1 | + | IgG2b, κ | KIS-1N |
| 2 | + | IgG2b, κ | |
| 3 | + | IgG2b, κ | |
| 4 | ± | IgG1, κ | KIS-2N |
| 5 | ± | IgG1, κ | |

Figure 4:
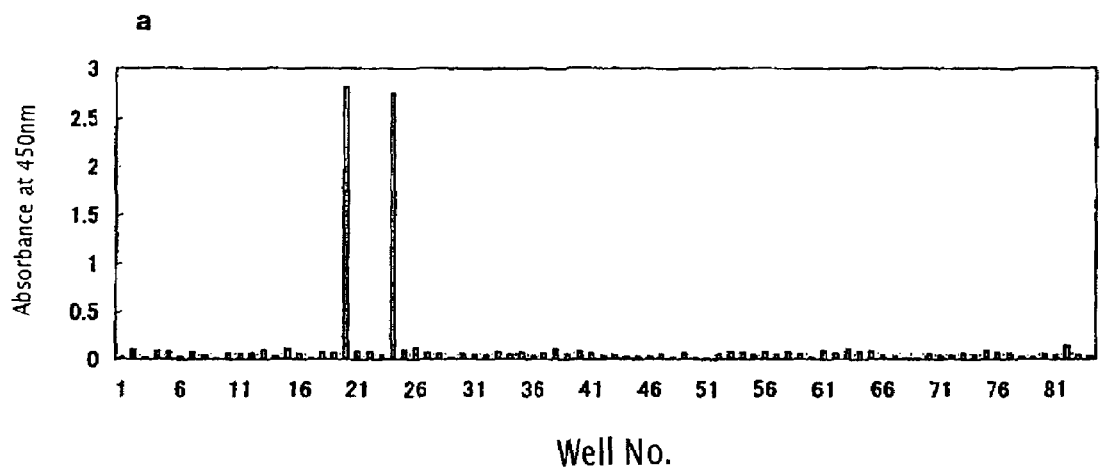
FIG. 4 shows a typical example of the screening of hybridoma after cell fusion when mouse immunized with [$Cys^{38}$] human metastin (38–54)-KLH was used.
Figure 4:
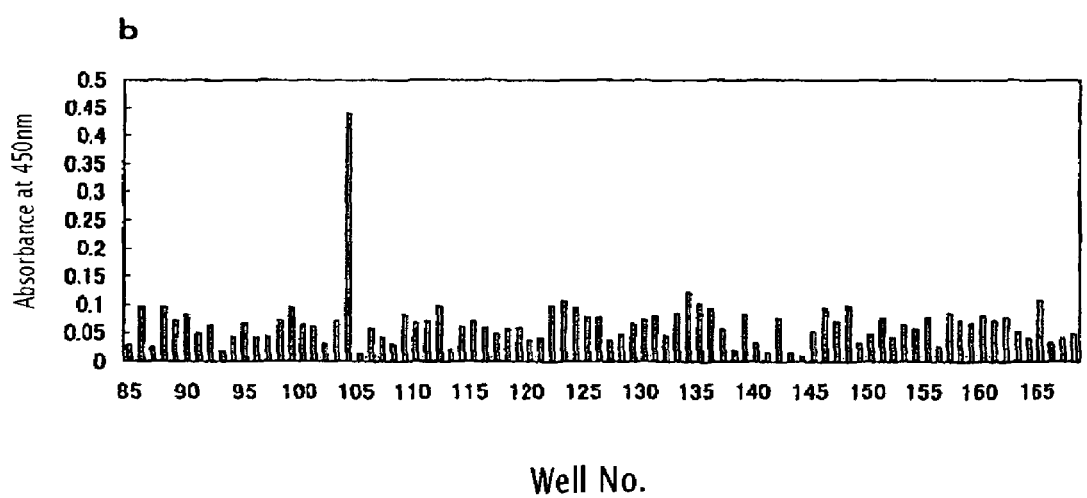

[1)]When 10 nM of human metastin (1–54) was present as an antigen:
+: (B/B$_0$) < 0.50
±: 0.50 ≤ (B/B$_0$) < 0.80
−: 0.80 ≤ (B/B$_0$)
B: The amount of HRP-labeled [Cys-NH$_2$$^{13}$] human metastin (1–13) bound to the antibody when the antigen was present
B$_0$: The amount of HRP-labeled [Cys-NH$_2$$^{13}$] human metastin (1–13) bound to the antibody when no antigen was present As an example of selecting the antibody producing cell lines of hybridomas derived from the mice immunized with [Cys$^{38}$] human metastin (38–54)-KLH, the results of antibody-producing conditions of the hybridoma obtained by cell fusion using mice Nos. 2 and 8 (cf. FIG. 2) are shown in FIG. 4. The 3 hybridomas below were selected from the antibody-producing hybridomas acquired (TABLE 2).

TABLE 2

Reactivity of anti-[Cys$^{38}$] human metastin (38–54) monoclonal antibody Reactivity[1)]

| Hybridoma No. | Human metastin (1–54) | Class/Subclass | Notes |
| --- | --- | --- | --- |
| 1 | + | IgG1, κ | KIS-1C |
| 2 | + | IgG1, κ | |
| 3 | ± | IgG1, κ | |

[1)]When 10 nM of human metastin (1–54) was present as an antigen:
+: (B/B$_0$) < 0.50
±: 0.50 ≤ (B/B$_0$) < 0.80
−: 0.80 ≤ (B/B$_0$)
B: The amount of HRP-labeled [Cys$^{38}$] human metastin (38–54) bound to the antibody when the antigen was present
B$_0$: The amount of HRP-labeled [Cys$^{38}$] human metastin (38–54) bound to the antibody when no antigen was present Next, these hybridomas were cloned by limiting dilution. In cloning, thymocytes from BALB/C mice were added as feeder cells in 5×10$^5$ cells/well. After cloning, the hybridomas were intraperitoneally injected to mice (BALB/C) in 1 to 3×10$^6$ cells/mouse, to which mice 0.5 ml of mineral oil had previously been given intraperitoneally. The ascites fluid containing the antibody was collected 6 to 20 days after.

The monoclonal antibody was purified from the ascites fluid obtained. That is, 6 to 20 ml of the ascites fluid was diluted with an equal volume of binding buffer [1.5M glycine containing 3.5M NaCl and 0.05% NaN$_3$ (pH 9.0)], and the dilution was applied on recombinant protein A-agarose (manufactured by Repligen) column, which had been previously equilibrated with the binding buffer. The specific antibody was eluted with an eluting buffer [0.1M citrate buffer containing 0.05% NaN$_3$ (pH 3.0)]. The eluate was dialyzed to PBS at 4° C. for 2 days, which was subjected to cell-free filtration through a filter of 0.22 μm (manufactured by Millipore) and then stored at 4° C. or −80° C.

In class/subclass determinations of monoclonal antibodies, enzyme-linked immunosorbent assay (ELISA) using purified monoclonal antibody-bound solid phase was used. That is, 100 μl each of 0.1M carbonate buffer (pH 9.6) solution containing 2 μg/ml of the antibody was dispensed on a 96-well microplate, which was allowed to stand at 4° C. for 24 hours. Following the procedure described in EXAMPLE 1, redundant binding sites in the wells were blocked with Block Ace. Thereafter, the class and subclass of immobilized antibodies were determined by ELISA using an isotyping kit (Mouse-Typer™ Sub-Isotyping Kit, manufactured by Biorad).

Experiment 14

Competitive Enzyme Immunoassay (1) Competitive Assay—EIA ([Cys-NH$_2$$^{13}$] Human Metastin (1–13) Monoclonal Antibody)

The reaction specificity was examined on the monoclonal antibodies prepared using [Cys$^{13}$-NH$_2$] human metastin (1–13)-KLH as the immunogen, by the following method.

First, the antibody titers of the respective solutions of monoclonal antibodies KIS-1Na and KIS-2Na were assayed by the method described in EXPERIMENT 13, and the antibody level (ca. 30 to 50 ng/ml) wherein the binding amount of a labeled form reaches about 50% of the saturation binding amount was determined as an antibody level used for competitive assay—EIA. Next, (i) 50 μl of the anti-metastin (1–12) antibody solution diluted with Buffer C to have 50 ng/ml of KIS-1Na, (ii) 50 μl of the human metastin (1–54) solution diluted with Buffer C, and (iii) 50 μl of the HRP-labeled [Cys$^{13}$-NH$_2$] human metastin (1–13) (diluted to 400-fold with Buffer C) obtained in EXPERIMENT 12 (1) described above were added to the anti-mouse immunoglobulin antibody-bound microplate described in EXPERIMENT 13, followed by reacting them at 4° C. for 16 hours. After the reaction, the plate was washed with PBS and the enzyme activity on the anti-mouse immunoglobulin antibody-bound microplate was assayed by the method described in EXPERIMENT 13 (1).

The results are shown in TABLE 1. It is understood therefrom that any one of the antibodies reacted with HRP-labeled [Cys$^{13}$-NH$_2$] human metastin (1–13) and also had reactivities with human metastin.

Figure 5:
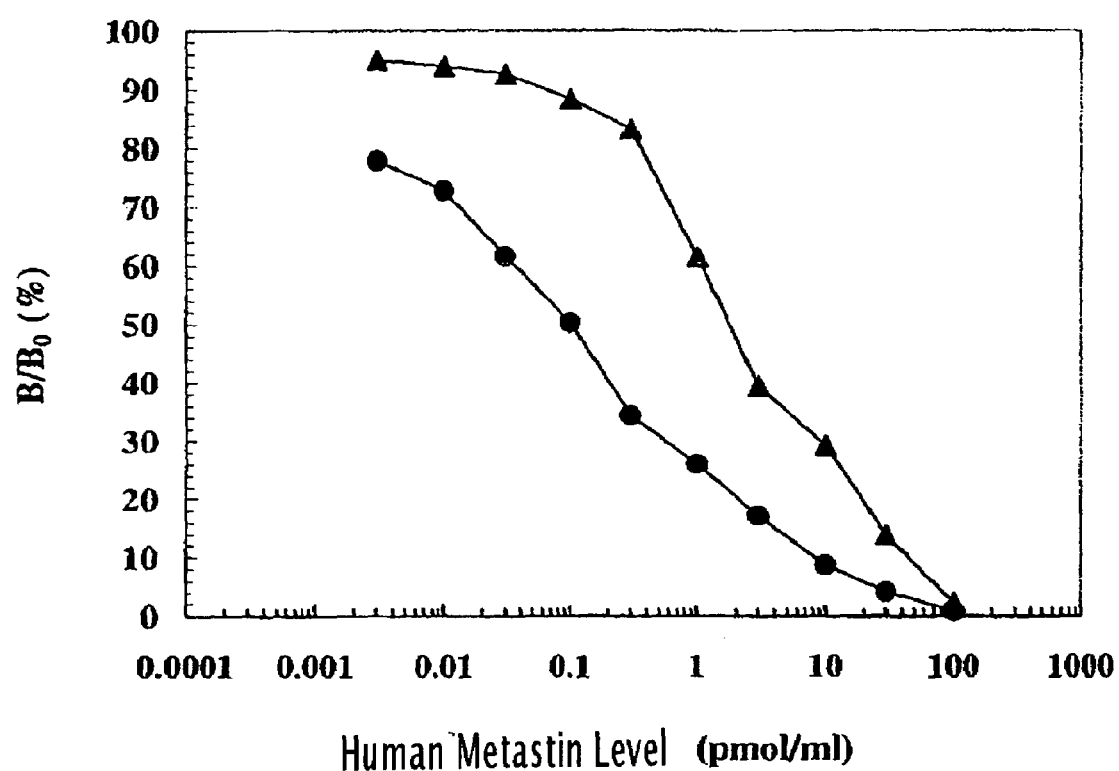
FIG. 5 shows the results of the reactivities on human metastin of monoclonal antibodies KIS-1Na (-●-) and KIS-2Na (-▲-) produced using [Cys-$NH_2$ $^{13}$] human metastin (1–13)-KLH as immunogen, which reactivities were evaluated by competitive EIA using HRP-labeled [Cys-$NH_2^{13}$] human metastin (1–13).

By way of illustration, the results of the competitive assay—EIA on the monoclonal antibody KIS-1Ca (IgG1, κ) showing the highest reactivity with human metastin are shown in FIG. 5.

From the standard curve of KIS-1Na for human metastin, the level of human metastin, which gave (B/B$_0$)=0.5, was found to be 0.1 nM, 0.058 ng/well (FIG. 5). Based on these results, it is considered that KIS-1Na strongly recognizes [Cys$^{13}$-NH$_2$] human metastin (1–13) and shows a high reactivity with human metastin.

(2) Competitive Assay—EIA ([Cys$^{38}$] Human Metastin (38–54) Monoclonal Antibody)

The reaction specificity of [Cys$^{38}$] human metastin (38–54) monoclonal antibody was examined in a similar manner.

First, the antibody titers of the respective monoclonal antibody solutions were assayed by the method described in EXPERIMENT 13 (2), and the antibody level (ca. 30 to 50 ng/ml) wherein the binding amount of a labeled form reaches about 50% of the saturation binding amount was determined as an antibody level used for competitive assay—EIA. Next, in the anti-mouse immunoglobulin antibody-bound microplate, (i) 50 μl of the anti-human metastin (39–54) antibody KIS-1Ca solution diluted with Buffer C to have 50 ng/ml and (ii) 50 μl of the HRP-labeled [Cys$^{38}$] human metastin (38–54) diluted to 500-fold with Buffer C described in EXPERIMENT 12 (2) were added to the wells, to which wells (iii) 50 μl of a Buffer C solution of 10$^{-6}$ M–10$^{-9}$ M human metastin or the partial peptide of human metastin [human metastin (1–54)-COOH (wherein the C-terminus is a carboxyl group), human metastin (40–54) represented by SEQ ID NO: 5, human metastin (45–54) represented by SEQ ID NO:6, human metastin (46–54) represented by SEQ ID NO:7, human metastin (47–54) represented by SEQ ID NO:8, or human metastin (48–54) represented by SEQ ID NO:9], diluted with Buffer C, which was followed by reacting them at 4° C. for 16 hours.

That is, the peptide described in (iii) was added one by one to the well where (i) and (ii) were present, whereby the reaction was carried out. After the reaction, the plate was washed with PBS and the enzyme activity on the solid phase was assayed by the method described in EXPERIMENT 13 (1).

The results are shown in TABLE 2. It is understood from the results that any of the antibodies reacted with HRP-labeled [Cys$^{38}$] human metastin (38–54) and had reactivities also with human metastin.

Figure 7:
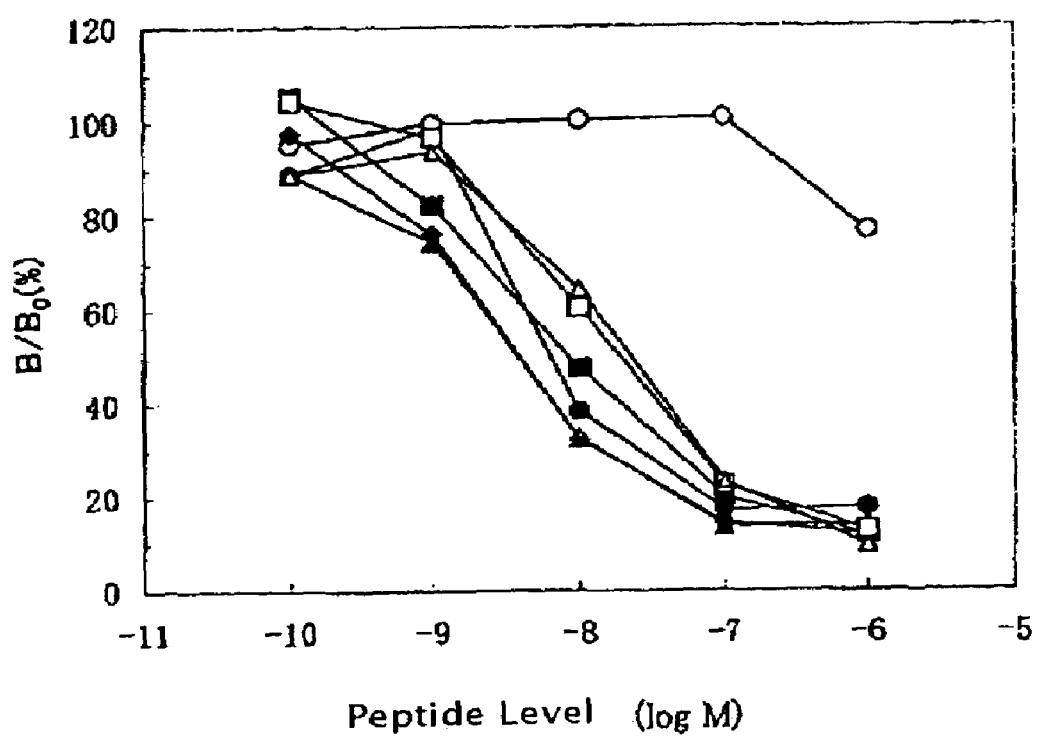
FIG. 7 shows the results of the reactivities of monoclonal antibody KIS-1Ca produced using [$Cys^{38}$] human metastin (38–54)-KLH as immunogen on human metastin (-●-), human metastin (1–54) COOH (-○-), human metastin (40–54) (-▲-), human metastin (45–54) (-◆-), human metastin (46–54) (-■-), human metastin (47–54) (-□-) and human metastin (48–54) (-Δ-), which reactivities were evaluated by competitive EIA using HRP-labeled [$Cys^{38}$] human metastin (38–54).

By way of illustration, the results of the competitive assay—EIA on the monoclonal antibody KIS-1Ca (IgG1, κ) showing the highest reactivity with human metastin are shown in FIG. 7.

Figure 6:
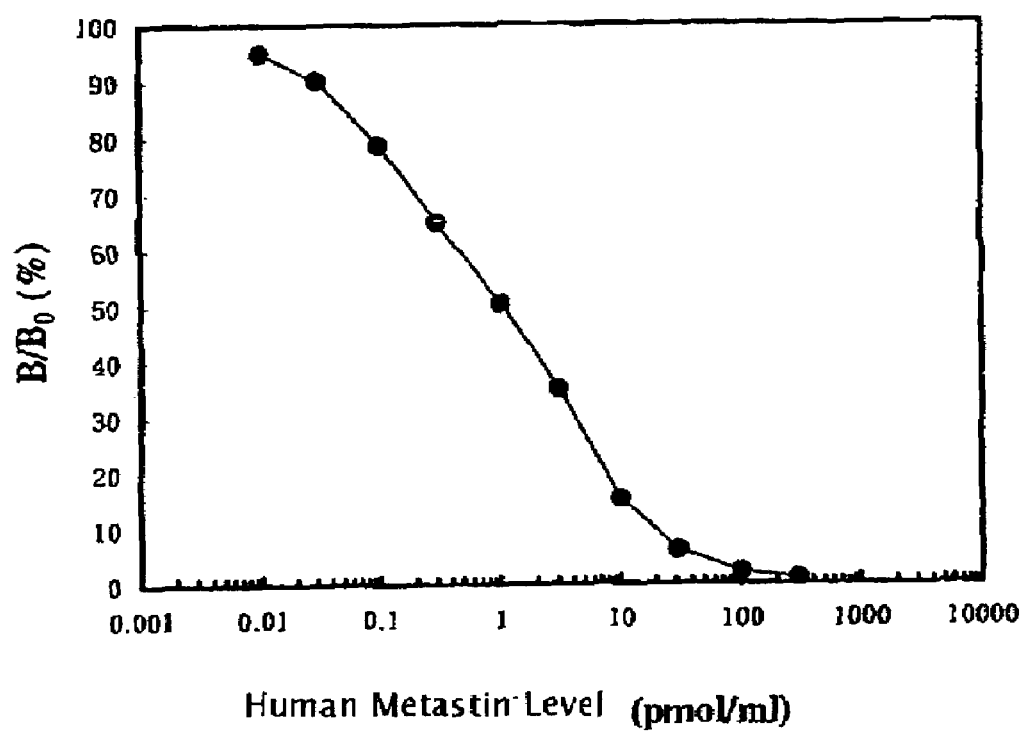
FIG. 6 shows the results of the reactivity on human metastin of monoclonal antibody KIS-1Ca produced using [$Cys^{38}$] human metastin (38–54)-KLH as immunogen, which reactivity was evaluated by competitive EIA using HRP-labeled [$Cys^{38}$] human metastin (38–54).

From the standard curve of KIS-1Ca for human metastin, the level of human metastin, which gave (B/B$_0$)=0.5, was found to be 1 nM, 0.58 ng/well (FIG. 6). This antibody KIS-1Ca showed some reactivity with human metastin (49–54), though it was weak, but showed no cross reactivity with metastin (1–54)-COOH. From the results, it is understood that the antibody KIS-1Ca strongly recognizes the C-terminal amide of human metastin at the C-terminus (FIG. 7).

Example 2

Preparation of HRP-Labeled Anti-Metastin Monoclonal Antibody (KIS-1Ca-HRP)

After 50 μl of DMF containing 0.77 μmol of GMBS was added to 0.1M phosphate buffer (pH 6.8) containing 9.56 mg (63.7 nmols) of the purified KIS-1Ca fraction, the mixture was reacted at room temperature for 40 minutes. The reaction solution was applied on a Sephadex G-25 column (eluant, 0.1M phosphate buffer, pH 6.7) for separation to give 7.17 mg of the maleimido-introduced antibody fraction. Next, 60 μl of DMF containing 6.67 μmols of N-succinimidyl-3-(2-pyrimidyldithio)propionate (SPDP) was added to 1.4 ml of 0.02M phosphate buffer (also containing 0.15M NaCl) (pH 6.8) containing 17.8 mg (445 nmols) of HRP, followed by reacting them at room temperature for 40 minutes. Subsequently, 0.4 ml of 0.1M acetate buffer (pH 4.5) containing 66 μmols of dithiothreitol was added. After reacting at room temperature for 20 minutes, the reaction mixture was applied on a Sephadex G-25 column (eluant, 0.1M phosphate buffer, pH 6.0, containing 2 mM EDTA) for separation to give 9.8 mg of SH-introduced HRP. Next, 8 mg of the SH-introduced HRP was mixed with 3 mg of the maleimido-introduced antibody fraction. After the mixture was concentrated to about 0.5 ml with Collodion Bag (manufactured by Sartorius K. K.), the concentrate was allowed to stand at 4° C. for 16 hours. The reaction solution was applied on Sephacryl S-300HR column (manufactured by Pharmacia) using 0.1M phosphate buffer, pH 6.5, as eluant. Thus, the KIS-1Ca-HRP complex fraction was purified.

Experiment 15

Sandwich Assay—EIA (Specificity and Sensitivity of Sandwich Assay—EIA)

After 100 µl each of 0.1M carbonate buffer (pH 9.6 solution) containing 15 µg/ml of the purified monoclonal antibody KIS-1Na obtained in EXAMPLE 1 was dispensed in a 96-well microplate, the plate was allowed to stand at 4° C. for 24 hours. The redundant binding sites in the wells were inactivated by adding 400 µl of Block Ace diluted with PBS to 4-fold.

To the plate prepared as described above, 100 µl of the human metastin standard solution diluted with 0.02M phosphate buffer (pH 7) containing Buffer C or peptides having the C-terminal F-$NH_2$ structure as in metastin [Calcitonin Gene Related Peptide (CGRP), Cholecystokinin-4 (CCK-4) and Prolactin-releasing Peptide 31 (PrRP31) (all purchased from Peptide Institute, Inc.)] was added, followed by reacting at 4° C. for 24 hours. After washing with PBS, 100 µl of KIS-1Ca-HRP (diluted to 20,000-fold with Buffer C) prepared in EXAMPLE 2 was added and the mixture was reacted at 4° C. for 24 hours, where the labeled form was used in a 30,000-fold dilution. After washing with PBS, the enzyme activity on the solid phase was assayed by the method described in EXPERIMENT 13 using TMB (enzyme reaction for 20 minutes).

Figure 8:
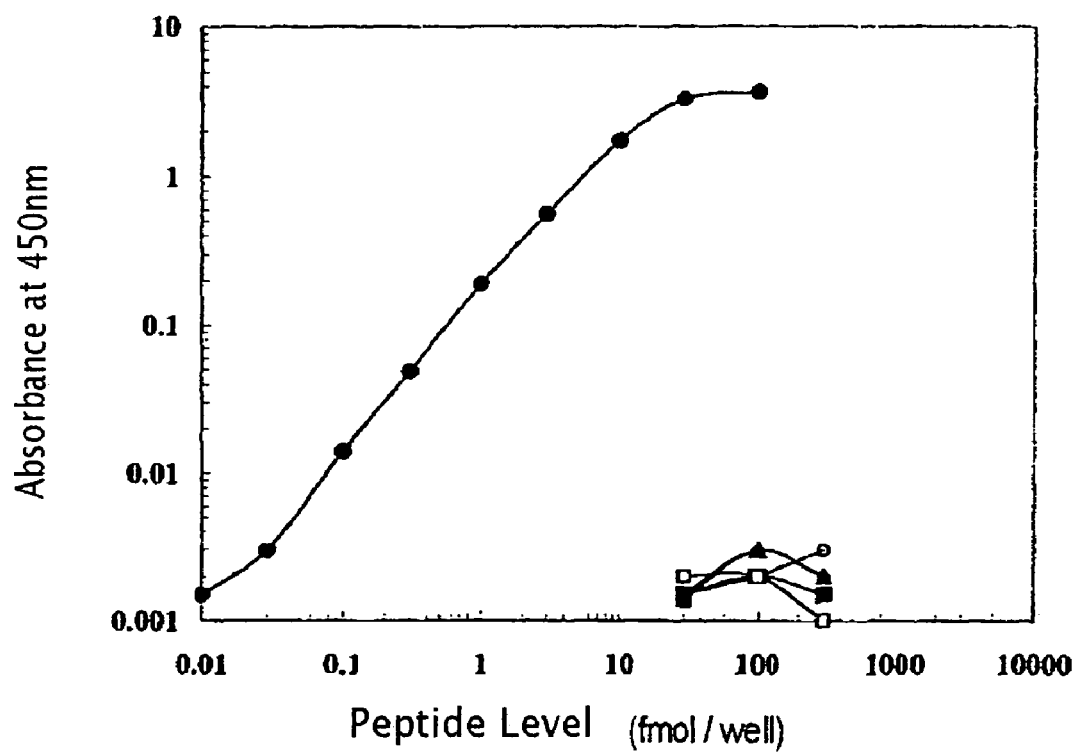
FIG. 8 shows standard curve of human metastin (-●-) obtained by sandwich EIA using KIS-1Ca-HRP as an enzyme-labeled antibody and KIS-1Na as an antibody for a solid phase. The figure further shows the reactivities with other peptides CGRP (-■-), CCK-4 (-▲-), NPFF (-◆-), PrRP31 (-○-) and AF-2 (-□-).

The results are shown in FIG. 8. The results revealed that human metastin was detected with an extremely high sensitivity.

That is, the sandwich assay—EIA enabled to detect human metastin in 0.3 fmol/well but detected none of the peptides, PrRP31, NPFF and AF-2 having the RF-$NH_2$ structure at the other C-terminus (FIG. 8). It was thus found that the sandwich assay—EIA using KIS-1Na as a solid phase and KIS-1Ca-HRP as a label can selectively detect human metastin with an extremely high sensitivity.

Experiment 16

Neutralizing Effect on the Biological Activity of Human Metastin by KIS-1Ca

The neutralizing activity on human metastin by KIS-1Ca was assayed with FLIPR (Molecular Devices) using as an indicator the intracellular Ca ion level increasing activity using hOT7T175 expression CHO cells described in JPA 2000-31259.

The hOT7T175 expression CHO cells were suspended in medium (10% dFBS-DMEM) in $1.2\times10^5$ cells/ml. A 200 µl aliquot of the suspension was plated on each well of a 96-well plate (Black plate clear bottom, Coster, Inc.) for FLIPR, using a dispenser ($4\times10^4$ cells/200 µl/well), and cultured at 37° C. overnight in a 5% $CO_2$ incubator, which was provided for use (hereinafter referred to as the cell plate). Then, 20 ml of FLIPR assay buffer [9.8 g of Nissui Hanks 2 (Nissui Seiyaku K. K.), 0.35 g of sodium hydrogencarbonate and 4.77 g of HEPES were rendered pH 7.4 with a sodium hydroxide solution, and the mixture was made 1 liter and subjected to a filter sterilization treatment] was mixed with 200 µl of 250 mM Probenecid and 210 µl of fetal bovine serum (FBS). Also, 2 vials (50 µg) of Fluo 3-AM (Dojin Kagaku Kenkyusho) was dissolved in 40 µl of dimethylsulfoxide and 40 µl of 20% Pluronic acid (Molecular Probe, Inc.). The solution was added to and mixed with Hanks'/HBSS-Probenecid-FBS described above, and 100 µl each of the resulting mixture was dispensed on each well of the cell plate, from which the medium was removed, using an 8 channel pipette. Incubation was performed in a 5% $CO_2$ incubator at 37° C. for an hour (dye loading). KIS-1Ca and anti-PrRP monoclonal antibody (P2L-1Ta) (H. Matsumoto et al.; Biochem. Biophys. Res. Commun., 257, 264–268 (1998)) as a control antibody, which has the same IgG subclass structure (IgG1, κ) as that of KIS-1Ca, were diluted with 120 µl of Hanks'/HBSS containing 2.5 mM Probenecid and 0.2% BSA. After incubation with human metastin ($1\times10^{-8}$ M) at 37° C. for an hour, 5 µl of each fraction was transferred to a 96-well plate (V-Bottom Plate, Coster, Inc.) for FLIPR (hereinafter, the sample plate). After completion of dye loading on the cell plate, the cell plate was washed 4 times with a wash buffer of Hanks'/HBSS supplemented with 2.5 mM Probenecid, using a plate washer (Molecular Devices). After washing, 100 µl of the wash buffer was left. The cell plate and the sample plate were set on FLIPR to perform assay (by FLIPR 50 µl of a sample was transferred from the sample plate to the cell plate).

Figure 9:
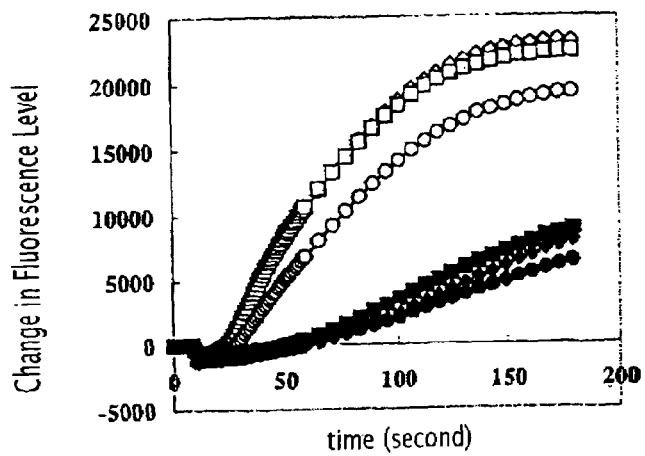
FIG. 9 shows the neutralizing activity of monoclonal antibody KIS-1Ca produced using [$Cys^{39}$] human metastin (39–54)-KLH as immunogen on the intracellular Ca ion level increasing activity using hOT7T175 expression CHO cells. The intracellular Ca ion level increasing activity after the reaction is shown in a) wherein KIS-1Ca or P2L-1T is reacted with human metastin (20 nM) in 1:1, b) wherein KIS-1Ca or P2L-1T is reacted with human metastin in 1:10, and c) wherein KIS-1Ca or P2L-1T is reacted with human metastin in 1:100, respectively. In the figure, symbols (-◇-), (-□-), (-○-), (-◆-), (-■-) and (-●-) represent P2L-1T (1), P2L-1T (2), P2L-1T (3), KIS-1C (1), KIS-1C (2) and KIS-1C (3), respectively.
Figure 9:
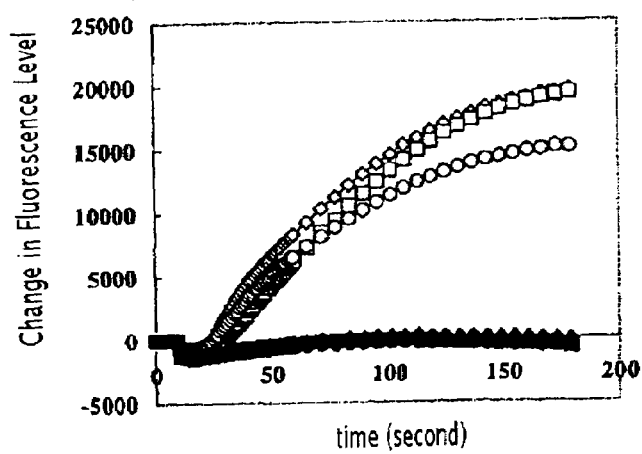
Figure 9:
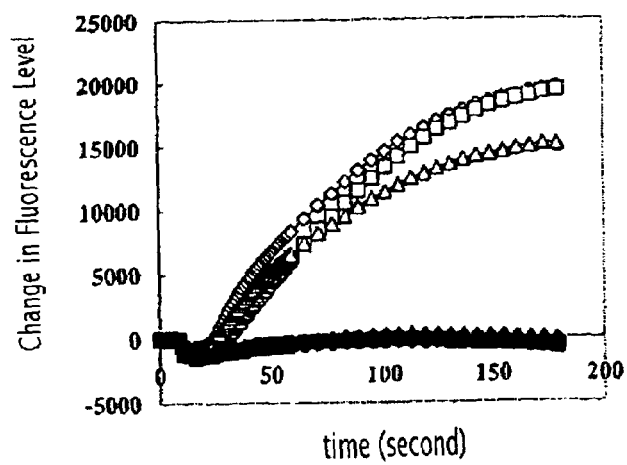

The results are shown in FIG. 9. It is understood from the results that KIS-1Ca inhibited the activity of human metastin by 70% in $2\times10^{-8}$ M and by 100% in $2\times10^{-7}$ M. On the other hand, it was only observed that P2L-1Ta inhibited the activity of human metastin by about 14% in $2\times10^{-6}$ M. The results above revealed that KIS-1Ca neutralized the intracellular [$Ca^{2+}$] increasing activity of human metastin.

Example 3

Quantification of Human Metastin in Plasma

Human plasma was diluted to 2-fold with an equal volume of Buffer C. Human metastin was quantified by the sandwich—EIA in EXPERIMENT 15 described above.

The results are shown in TABLE 3.

TABLE 3

| | Immunoreactive Human Metastin | |
|---|---|---|
| No. | Male (fmol/ml) | Female (fmol/ml) |
| 1 | 1.64 | 1.65 |
| 2 | 1.51 | 12.7 |
| 3 | 1.72 | 1.27 |
| 4 | 1.07 | 8.35 |
| 5 | 0.79 | |
| 6 | 0.91 | |
| 7 | 2.18 | |
| 8 | 0.88 | |
| 9 | 1.74 | |
| 10 | 1.02 | |
| 11 | 0.59 | |
| 12 | 1.59 | |
| 13 | 3.59 | |

Level of human metastin in human plasma (1 ml):
Male: 1.48 ± 0.22 fmol/ml (mean ± SEM, n = 13)
Female: 6.00 ± 2.77 fmol/ml (mean ± SEM, n = 13)

Level of human metastism in human plasma (1 ml):
 Male: 1.48±0.22 fmol/ml (mean±SEM, n=13)
 Female: 6.00±2.77 fmol/ml (mean±SEM, n=4)

Example 4

Detection of Human Metastin in Human Plasma by Reverse Phase High Performance Liquid Chromatography (RP-HPLC)

To quantify the immunological activity of human metastin contained in human plasma, which was described in EXAMPLE 3, 15 ml of acetonitrile was added to and mixed with 5 ml of human plasma. The mixture was centrifuged to remove proteins. After the supernatant was lyophilized, this fraction was concentrated followed by fractionation on reverse phase HPLC using ODS-80™.

Column Conditions:
 Column: ODS-80™ (4.6×250 mm)
Eluants: Eluant A (5% acetonitrile containing 0.05% trifluoroacetic acid)
 Eluant B (60% acetonitrile containing 0.05% trifluoroacetic acid)
Elution Method: The acetonitrile concentration was increased from 5% to 30% for the initial 5 minutes and then linearly increased to 30–40% over 30 minutes.
 Flow rate: 1.0 ml/min. Fractionation: 0.5 ml/tube After the eluted fraction was lyophilized, the lyophilized product was dissolved in 250 µl of Buffer C and the solution was provided for the sandwich assay—EIA described in EXPERIMENT 15.

Figure 10:
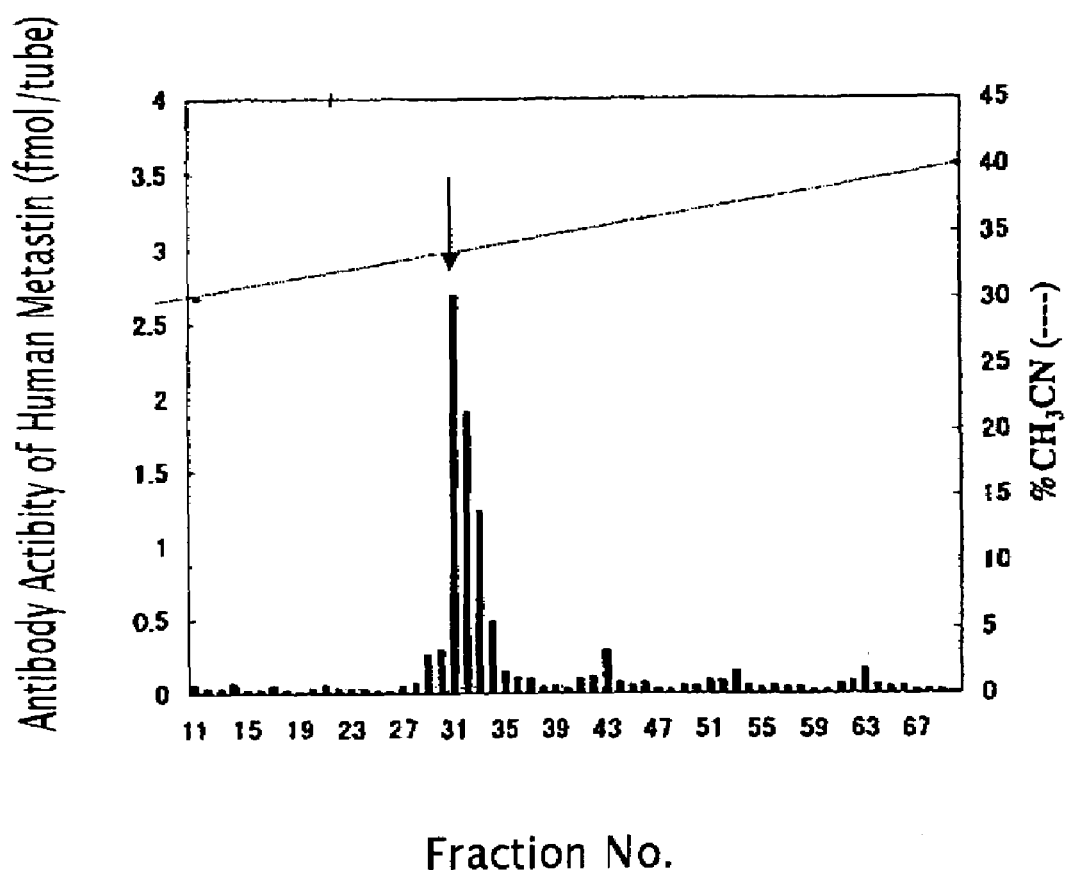
FIG. 10 shows the results of the immunological activity of human metastin in the fractions eluted from human plasma, which was quantified on reverse phase HPLC by sandwich EIA using KIS-1Ca-HRP as an enzyme-labeled antibody and KIS-1Na as an antibody for a solid phase, wherein broken line (----) denotes an acetonitrile gradient.

The results are shown in FIG. 10. The immunological activity of human metastin in plasma was detected almost at the eluted position of human metastin (recovery rate of 102%). Thus, it was confirmed that the sandwich assay—EIA detected human metastin.

From the results it is understood that this assay system can be an important means for studying the change of human metastin in plasma.

Example 5

Quantification of Human Metastin in Plasma of Pregnant Women

Plasma from pregnant women collected in each week of pregnancy was diluted to 2-fold with an equal volume of Buffer C, and human metastin was quantified by the sandwich assay—EIA described in EXPERIMENT 15 above. The plasma of pregnant women was purchased from DCP, Inc. and met the informed consent.

The results are shown in TABLE 4.

TABLE 4

| No. | 4–10 W (fmol/ml) | 11–20 W (fmol/ml) | 21–30 W (fmol/ml) | 31–40 W (fmol/ml) | Post (fmol/ml) |
|---|---|---|---|---|---|
| 1 | 99.0 | 1598 | 1706 | 3441 | 7.80 |
| 2 | 283 | 3613 | 5351 | 11035 | 3.80 |
| 3 | 63.6 | 2065 | 22805 | 6928 | 5.76 |
| 4 | 10.8 | 3100 | 6218 | 11532 | 11.4 |
| Mean | 114 | 2594 | 12860 | 8234 | 7.19 |
| SEM | 59.3 | 462 | 4253 | 1901 | 1.62 |

Post denotes 4 or 5 days after delivery.

From TABLE 4, it is considered that the human metastin level in blood would increase with pregnancy and would revert to a normal level after delivery. When compared to the level in non-pregnancy of women (6.00±2.77 fmols/ml), the human metastin level increased by about 20 times at the beginning pregnancy (4–10th weeks) and increased by about 2000 times during the 21–30th weeks). These results indicate that human metastin is produced in the placenta, the human metastin level in blood can be used as an indicator of pregnancy, and the monoclonal antibody of the present invention is useful as a clinical diagnostic.

Example 6

Quantification of Human Metastin in Plasma of the Umbilical Artery and Umbilical Vein Plasma of the umbilical artery and umbilical vein obtained during childbirth was diluted to 2-fold with an equal volume of Buffer C, and human metastin was quantified by the sandwich-EIA in EXPERIMENT 15 described above. The plasma of pregnant woman was purchased from DCP, Inc. and met the informed consent.

The results are shown in TABLE 5.

TABLE 5

| | Immunoreactive human metastin | |
|---|---|---|
| No. | Umbilical Artery (fmol/ml) | Umbilical Vein (fmol/ml) |
| 1 | 469 | 543 |
| 2 | 406 | 401 |
| 3 | 347 | 749 |
| 4 | 674 | 775 |
| Mean | 449 | 497 |
| SEM | 60.3 | 139 |

The results revealed that it was possible to determine the metastin level in special blood like cord blood, and metastin was present in the cord blood as well. Thus, the antibody of the present invention is considered to be applicable to diagnosis for abnormalities of fetuses or newborn infants.

In TABLE 5, no difference in the metastin blood level is noted between the umbilical artery and the umbilical vein, suggesting a poor possibility that fetuses would produce metastin.

Example 7

Immunohistochemical Staining for Metastin of Human Placenta Using KIS-1Ca

A paraffin section of human placenta slide (purchased from DAKO) was deparaffinized. Specifically, the slide was immersed in xylene for 5 minutes twice, and then in 100% ethanol for 5 minutes twice. Thereafter, the slide was immersed for 5 minutes each sequentially in 90% ethanol, 80% ethanol and 70% ethanol, and then immersed in PBS for 5 minutes twice. The slide was heat-treated in 1 mM EDTA buffer (pH 8.0) at 95° C. for 30 minutes in an autoclave. After washing with PBS containing 0.3% Triton X100 (PBT) for 5 minutes twice, KIS-1Ca diluted to 60 µg/ml with 1.5% horse serum-containing PBT (PBS containing 1% normal horse serum and 0.4% Triton X-100) was added to the slide. The reaction was carried out at 4° C. for 16 hours and the slide was washed 3 times with PBT. Biotin-labeled anti-mouse IgG antibody was added to the slide, followed by reacting at room temperature for 30 minutes. After washing twice with PBT, an avidin-biotinated peroxidase solution was added to react them at room temperature for 30 minutes (Vectastain (mouse IgG) ABC Kit, Funakoshi Co., Ltd.). After the slide was washed 4 times with PBT, the peroxidase was visualized to produce a color using a diaminobenzidine (3,3-diaminobenzidine-tetrachloride) substrate kit (Funakoshi Co., Ltd.), and the reaction was terminated 2 to 10 minutes after. Immunopositive reaction was detected on syncytiotrophoblast of the placenta, which revealed that KIS-1Ca is available for Immunohistochemical staining of metastin.

INDUSTRIAL APPLICABILITY

Human metastin is a peptide isolated from the placenta as an endogenous ligand of orphan receptor hOT7T175 and shows a chemotactic inhibition activity and a cancer metastasis suppression activity. Further investigations are necessary for the physiological functions of human metastin. The antibody of the present invention possesses extremely high binding ability to human metastin or its derivatives and can neutralize the intracellular $[Ca^{2+}]$ increasing activity of human metastin or its derivatives. Further by suppressing the actions of human metastin or derivatives thereof, the carcinostatic activity, and so forth can be expected. Also, when cancers in which human metastin or its derivatives are expressed are identified, an anti-cancer treatment can be made by missile therapy using the antibody of the present invention. Human metastin or its derivatives can be quantified specifically by immunological sandwich assay with a high sensitivity, in which the monoclonal antibody recognizing the C-terminus of human metastin and the monoclonal antibody recognizing the N-terminus of human metastin. Thus, human metastin or its derivatives are useful for clarification of the physiological functions of human metastin or its derivatives and pathological conditions. Furthermore, by determining a level of human metastin or its derivatives in blood, human metastin or its derivatives are also applicable to diagnosis of, for example, cancers (e.g., skin cancer, breast cancer, colorectal cancer, colon cancer, prostate cancer, thyroid cancer, lung cancer, cervical cancer, and so forth), pregnancy induced hypertension, placental hypoplasia, threatened abortion, endometriosis, infertility, polycystic ovary syndrome, and so forth, or pregnancy, and so forth. Also, the antibody of the present invention is useful as the agent for the prevention/treatment of diseases associated with human metastin or its derivatives [for example, cancers (e.g., skin cancer, breast cancer, colorectal cancer, colon cancer, prostate cancer, thyroid cancer, lung cancer, cervical cancer, and so forth), pregnancy induced hypertension, placental hypoplasia, threatened abortion, endometriosis, infertility, polycystic ovary syndrome, and so forth]; moreover, the antibody is useful for prevention of premature delivery and for reducing labor pain. In addition, the antibody of the present invention is available for immunohistochemical staining of metastin.

The invention claimed is:

1. An isolated monoclonal antibody named KIS-1Ca that is produced by the hybridoma cell line deposited with the International Patent Organisms Depository (IPOD) as accession number FERM BP-7430.

2. An isolated monoclonal antibody wherein the isolated monoclonal antibody:
   (i) is capable of specifically reacting with the C-terminal region of SEQ ID NO: 1, wherein the C-terminal region consists of SEQ ID NO: 6,
   (ii) has a neutralizing activity to a peptide having the amino acid sequence of SEQ ID NO: 1, SEQ ID NO: 3, SEQ ID NO: 5, SEQ ID NO: 6, SEQ ID NO: 7, SEQ ID NO: 8, or SEQ ID NO: 9, and
   (iii) is named Kis-1Ca and is produced by the hybridoma cell line deposited with the International Patent Organisms Depository (IPOD) as accession number FERM BP-7430.

3. The antibody according to claim 1 or claim 2, which is labeled.

4. The hybridoma cell line deposited with the International Patent Organisms Depository (IPOD) as accession number FERM BP-7430.

5. The hybridoma cell line producing the monoclonal antibody according to claim 1 or claim 2, which is deposited with the International Patent Organisms Depository (IPOD) as accession number FERM BP-7430.

* * * * *

UNITED STATES PATENT AND TRADEMARK OFFICE
CERTIFICATE OF CORRECTION

| | | |
|---|---|---|
| PATENT NO. | : 7,112,662 B2 | Page 1 of 1 |
| APPLICATION NO. | : 10/490125 | |
| DATED | : September 26, 2006 | |
| INVENTOR(S) | : Hirokazu Matsumoto et al. | |

It is certified that error appears in the above-identified patent and that said Letters Patent is hereby corrected as shown below:

Title Page item 54 and col. 1 line 1

Delete: "ANTI-METASIN ANTIBODIES AND THEIR METHODS OF USE"
Add: --ANTI-METASTIN ANTIBODIES AND THEIR METHODS OF USE--

Column 38, Line 35-36

Delete - "The antibody according to claim 1 or claim 2, which is labeled."
Add -- A labeled antibody wherein the antibody according to claim 8 or claim 15 is labeled.--

Signed and Sealed this

Twenty-fifth Day of December, 2007

JON W. DUDAS
*Director of the United States Patent and Trademark Office*

```
                            SEQUENCE LISTING

<160> NUMBER OF SEQ ID NOS: 9

<210> SEQ ID NO 1
<211> LENGTH: 54
<212> TYPE: PRT
<213> ORGANISM: human
<220> FEATURE:
<221> NAME/KEY: misc_binding
<222> LOCATION: (54)
<223> OTHER INFORMATION: the C-terminal of the polypeptide is amide

<400> SEQUENCE: 1

Gly Thr Ser Leu Ser Pro Pro Glu Ser Ser Gly Ser Arg Gln Gln
  1               5                  10                  15

Pro Gly Leu Ser Ala Pro His Ser Arg Gln Ile Pro Ala Pro Gln Gly
                 20                  25                  30

Ala Val Leu Val Gln Arg Glu Lys Asp Leu Pro Asn Tyr Asn Trp Asn
             35                  40                  45

Ser Phe Gly Leu Arg Phe
         50

<210> SEQ ID NO 2
<211> LENGTH: 13
<212> TYPE: PRT
<213> ORGANISM: human
<220> FEATURE:
<221> NAME/KEY: misc_binding
<222> LOCATION: (13)
<223> OTHER INFORMATION: the C-terminal of the polypeptide is amide

<400> SEQUENCE: 2

Gly Thr Ser Leu Ser Pro Pro Glu Ser Ser Gly Cys
  1               5                  10
```

```
<210> SEQ ID NO 3
<211> LENGTH: 17
<212> TYPE: PRT
<213> ORGANISM: human
<220> FEATURE:
<221> NAME/KEY: misc_binding
<222> LOCATION: (17)
<223> OTHER INFORMATION: the C-terminal of the polypeptide is amide

<400> SEQUENCE: 3

Cys Glu Lys Asp Leu Pro Asn Tyr Asn Trp Asn Ser Phe Gly Leu Arg
 1               5                  10                  15

Phe

<210> SEQ ID NO 4
<211> LENGTH: 54
<212> TYPE: PRT
<213> ORGANISM: human

<400> SEQUENCE: 4

Gly Thr Ser Leu Ser Pro Pro Glu Ser Ser Gly Ser Arg Gln Gln
 1               5                  10                  15

Pro Gly Leu Ser Ala Pro His Ser Arg Gln Ile Pro Ala Pro Gln Gly
                20                  25                  30

Ala Val Leu Val Gln Arg Glu Lys Asp Leu Pro Asn Tyr Asn Trp Asn
         35                  40                  45

Ser Phe Gly Leu Arg Phe
     50

<210> SEQ ID NO 5
<211> LENGTH: 15
<212> TYPE: PRT
<213> ORGANISM: humnan
<220> FEATURE:
<221> NAME/KEY: misc_binding
<222> LOCATION: (15)
<223> OTHER INFORMATION: the C-terminal of the polypeptide is amide

<400> SEQUENCE: 5

Lys Asp Leu Pro Asn Tyr Asn Trp Asn Ser Phe Gly Leu Arg Phe
 1               5                  10                  15

<210> SEQ ID NO 6
<211> LENGTH: 10
<212> TYPE: PRT
<213> ORGANISM: humnan
<220> FEATURE:
<221> NAME/KEY: misc_binding
<222> LOCATION: (10)
<223> OTHER INFORMATION: the C-terminal of the polypeptide is amide

<400> SEQUENCE: 6

Tyr Asn Trp Asn Ser Phe Gly Leu Arg Phe
 1               5                  10

<210> SEQ ID NO 7
<211> LENGTH: 9
<212> TYPE: PRT
<213> ORGANISM: humnan
<220> FEATURE:
<221> NAME/KEY: misc_binding
<222> LOCATION: (9)
<223> OTHER INFORMATION: the C-terminal of the polypeptide is amide

<400> SEQUENCE: 7

Asn Trp Asn Ser Phe Gly Leu Arg Phe
```

-continued

```
<210> SEQ ID NO 8
<211> LENGTH: 8
<212> TYPE: PRT
<213> ORGANISM: humnan
<220> FEATURE:
<221> NAME/KEY: misc_binding
<222> LOCATION: (8)
<223> OTHER INFORMATION: the C-terminal of the polypeptide is amide

<400> SEQUENCE: 8

Trp Asn Ser Phe Gly Leu Arg Phe
 1               5

<210> SEQ ID NO 9
<211> LENGTH: 7
<212> TYPE: PRT
<213> ORGANISM: humnan
<220> FEATURE:
<221> NAME/KEY: misc_binding
<222> LOCATION: (7)
<223> OTHER INFORMATION: the C-terminal of the polypeptide is amide

<400> SEQUENCE: 9

Asn Ser Phe Gly Leu Arg Phe
 1               5
```